(12) United States Patent
Cao et al.

(10) Patent No.: US 12,714,327 B2
(45) Date of Patent: Aug. 25, 2026

(54) MAGNETIC POSITION SENSOR AND CABLE

(71) Applicant: St. Jude Medical International Holding S. à. r.l., Luxembourg (LU)

(72) Inventors: Hong Cao, Maple Grove, MN (US); Bruce Ebner, Shorewood, MN (US); Vladislav Dmidrievich Popov, Plymouth, MN (US); Aditi Mitkar, Minnetonka, MN (US); Derek C. Sutermeister, Ham Lake, MN (US)

(73) Assignee: St. Jude Medical International Holding S.à. r.l., Luxembourg (LU)

( * ) Notice: Subject to any disclaimer, the term of this patent is extended or adjusted under 35 U.S.C. 154(b) by 367 days.

(21) Appl. No.: 18/133,979

(22) Filed: Apr. 12, 2023

(65) Prior Publication Data

US 2023/0329577 A1 Oct. 19, 2023

Related U.S. Application Data

(60) Provisional application No. 63/399,992, filed on Aug. 22, 2022, provisional application No. 63/330,658, filed on Apr. 13, 2022.

(51) Int. Cl.
*A61B 5/06* (2006.01)
*A61M 25/01* (2006.01)

(52) U.S. Cl.
CPC ............. *A61B 5/062* (2013.01); *A61M 25/01* (2013.01)

(58) Field of Classification Search
CPC ...................................................... A61B 5/062
See application file for complete search history.

(56) References Cited

U.S. PATENT DOCUMENTS

| | | | |
|---|---|---|---|
| 4,522,212 | A | 6/1985 | Gelinas et al. |
| 5,224,939 | A | 7/1993 | Holman et al. |
| 5,380,301 | A | 1/1995 | Prichard et al. |
| 5,400,783 | A | 3/1995 | Pomeranz et al. |
| 5,456,254 | A | 10/1995 | Pietroski et al. |
| 5,626,136 | A | 5/1997 | Webster, Jr. |
| 5,702,438 | A | 12/1997 | Avitall |

(Continued)

FOREIGN PATENT DOCUMENTS

| | | | |
|---|---|---|---|
| AU | 2015202258 | A1 | 5/2015 |
| AU | 2016204351 | A1 | 1/2017 |

(Continued)

*Primary Examiner* — Rochelle D Turchen
(74) *Attorney, Agent, or Firm* — Kilpatrick Townsend & Stockton LLP

(57) ABSTRACT

Magnetic position sensors include features to enhance performance and durability. In many embodiments, a magnetic position sensor includes a magnetically permeable core and a coil. The core has a central axis and a core length along the central axis. The coil is configured to generate output an electric signal in response to a magnetic field. The coil has a coil length along the central axis that is less than the core length. In some embodiments, a magnetic position sensor includes a magnetically permeable core, a coil, a pair of signal wires, and a third wire. The coil is configured to output an electric signal in response to a magnetic field. The pair of signal wires is connected to and extends from the coil. The third wire extends along a length of the pair of signal wires and is configured to reinforce the pair of signal wires.

20 Claims, 7 Drawing Sheets

(56) References Cited

U.S. PATENT DOCUMENTS 5,715,817 A 2/1998 Stevens-Wright et al.
5,715,832 A 2/1998 Koblish et al.
5,827,278 A 10/1998 Webster, Jr.
5,876,373 A 3/1999 Giba et al.
5,964,757 A 10/1999 Ponzi
6,029,091 A 2/2000 de la Rama et al.
6,071,282 A 6/2000 Fleischman
6,074,379 A 6/2000 Prichard
6,123,699 A 9/2000 Webster, Jr.
6,171,277 B1 1/2001 Ponzi
6,183,463 B1 2/2001 Webster, Jr.
6,198,974 B1 3/2001 Webster, Jr.
6,210,407 B1 4/2001 Webster
6,233,476 B1 5/2001 Strommer et al.
6,267,746 B1 7/2001 Bumbalough
6,273,404 B1 8/2001 Holman et al.
6,415,187 B1 7/2002 Kuzma et al.
6,491,681 B1 12/2002 Kunis et al.
6,522,932 B1 2/2003 Kuzma et al.
6,554,794 B1 4/2003 Mueller et al.
6,556,695 B1 4/2003 Packer et al.
6,652,515 B1 11/2003 Maguire et al.
6,658,302 B1 12/2003 Kuzma et al.
6,961,602 B2 11/2005 Fuimaono et al.
7,004,937 B2 2/2006 Lentz et al.
7,027,851 B2 4/2006 Mejia
7,089,045 B2 8/2006 Fuimaono et al.
7,099,712 B2 8/2006 Fuimaono et al.
7,214,220 B2 5/2007 McGlinch et al.
7,217,256 B2 5/2007 Di Palma
7,228,164 B2 6/2007 Fuimaono et al.
7,257,435 B2 8/2007 Plaza
7,365,745 B2 4/2008 Olson
7,412,274 B2 8/2008 Mejia
7,429,261 B2 9/2008 Kunis et al.
7,561,907 B2 7/2009 Fuimaono et al.
7,608,063 B2 10/2009 Le et al.
7,625,365 B2 12/2009 McGlinch et al.
7,666,204 B2 2/2010 Thornton et al.
7,774,051 B2 8/2010 Voth
7,825,925 B2 11/2010 Voth
7,885,707 B2 2/2011 Hauck
7,894,871 B2 2/2011 Wittkampf et al.
7,959,601 B2 6/2011 McDaniel et al.
7,985,215 B2 7/2011 Guo et al.
7,988,639 B2 8/2011 Starks
8,038,625 B2 10/2011 Afonso et al.
8,103,327 B2 1/2012 Harlev et al.
8,130,221 B2 3/2012 Voth
8,137,321 B2 3/2012 Argentine
8,157,848 B2 4/2012 Zhang et al.
8,221,390 B2 7/2012 Pal et al.
8,229,545 B2 7/2012 Afonso
8,253,725 B2 8/2012 Voth
8,271,099 B1 9/2012 Swanson
8,273,016 B2 9/2012 O'Sullivan
8,352,019 B2 1/2013 Starks
8,364,253 B2 1/2013 Voth
8,376,990 B2 2/2013 Ponzi et al.
8,391,947 B2 3/2013 Urman et al.
8,447,377 B2 5/2013 Harlev et al.
8,454,538 B2 6/2013 Wittkampf et al.
8,454,589 B2 6/2013 Deno et al.
8,486,063 B2 7/2013 Werneth et al.
8,565,894 B2 10/2013 Vetter et al.
8,603,069 B2 12/2013 Selkee
8,608,703 B2 12/2013 Riles et al.
8,620,978 B2 12/2013 Koyrakh
8,647,284 B2 2/2014 Afonso
8,649,880 B1 2/2014 Parker, Jr.
8,700,120 B2 4/2014 Koblish
8,706,193 B2 4/2014 Govari et al.
8,744,599 B2 6/2014 Tegg
8,755,861 B2 6/2014 Harlev et al.
8,771,267 B2 7/2014 Kunis et al.
8,777,929 B2 7/2014 Schneider et al.
8,792,962 B2 7/2014 Esguerra et al.
8,805,490 B2 8/2014 Hauck
8,814,824 B2 8/2014 Kauphusman et al.
8,814,825 B2 8/2014 Tegg et al.
8,825,144 B2 9/2014 Starks
8,849,393 B2 9/2014 Hauck et al.
8,882,705 B2 11/2014 McDaniel et al.
8,894,610 B2 11/2014 Macnamara et al.
8,979,841 B2 3/2015 Kunis et al.
8,996,091 B2 3/2015 de la Rama et al.
9,017,308 B2 4/2015 Klisch et al.
9,026,196 B2 5/2015 Curran et al.
9,033,917 B2 5/2015 Magana et al.
9,044,245 B2 6/2015 Condie et al.
9,050,010 B2 6/2015 Bui et al.
9,078,591 B2 7/2015 Wittkampf et al.
9,101,733 B2 8/2015 McDaniel
9,111,175 B2 8/2015 Strommer et al.
9,113,807 B2 8/2015 Schweitzer et al.
9,137,611 B2 9/2015 Unno et al.
9,159,162 B2 10/2015 Carbonera et al.
9,198,601 B2 12/2015 Hauck et al.
9,204,927 B2 12/2015 Afonso et al.
9,204,929 B2 12/2015 Solis
9,216,056 B2 12/2015 Datta et al.
9,237,920 B2 1/2016 Leo et al.
9,247,990 B2 2/2016 Kauphusman et al.
9,326,815 B2 5/2016 Watson
9,339,325 B2 5/2016 Miller et al.
9,339,631 B2 5/2016 Graham et al.
D761,313 S 7/2016 Quinn et al.
D761,808 S 7/2016 Quinn et al.
9,392,973 B2 7/2016 Curran et al.
9,433,751 B2 9/2016 Ponzi et al.
9,433,752 B2 9/2016 Jimenez et al.
9,468,495 B2 10/2016 Kunis et al.
9,474,486 B2 10/2016 Eliason et al.
9,486,152 B2 11/2016 Craven et al.
9,486,280 B2 11/2016 Koblish et al.
9,486,282 B2 11/2016 Solis
9,522,035 B2 12/2016 Highsmith
9,532,703 B2 1/2017 Huszar et al.
9,539,413 B2 1/2017 Ogle
9,549,689 B2 1/2017 Olson
9,560,988 B2 2/2017 Carbonera et al.
9,585,586 B2 3/2017 Koyrakh et al.
9,591,990 B2 3/2017 Chen et al.
9,597,036 B2 3/2017 Aeby et al.
9,610,027 B2 4/2017 Hauck et al.
9,629,675 B2 4/2017 Kleshinski et al.
9,649,158 B2 5/2017 Datta et al.
9,687,166 B2 6/2017 Subramaniam et al.
9,693,733 B2 7/2017 Altmann et al.
9,694,159 B2 7/2017 Schneider et al.
9,694,161 B2 7/2017 Selkee
9,713,418 B2 7/2017 Huszar et al.
9,788,895 B2 10/2017 Solis
9,808,171 B2 11/2017 Balachandran et al.
9,820,664 B2 11/2017 Hoitink et al.
9,833,608 B2 12/2017 Masson
9,844,645 B2 12/2017 Pai et al.
9,848,795 B2 12/2017 Marecki et al.
9,907,480 B2 3/2018 Basu et al.
9,919,132 B2 3/2018 Tegg et al.
9,949,656 B2 4/2018 Wu et al.
9,956,049 B2 5/2018 Shmarak et al.
9,986,949 B2 6/2018 Govari et al.
10,004,877 B2 6/2018 Tegg
10,034,637 B2 7/2018 Harlev et al.
10,052,457 B2 8/2018 Nguyen et al.
10,065,019 B2 9/2018 Hamuro et al.
10,099,036 B2 10/2018 Heideman et al.
10,118,022 B2 11/2018 Helgeson et al.
10,130,423 B1 11/2018 Viswanathan et al.
10,136,829 B2 11/2018 Deno et al.
10,143,394 B2 12/2018 Solis
10,172,673 B2 1/2019 Viswanathan et al.
10,278,614 B2 5/2019 Curran et al.

(56) References Cited

U.S. PATENT DOCUMENTS 10,285,610 B2 5/2019 Wu
10,322,261 B2 6/2019 Pai et al.
10,362,952 B2 7/2019 Basu et al.
10,362,954 B2 7/2019 de la Rama et al.
10,376,170 B2 8/2019 Quinn et al.
10,384,036 B2 8/2019 Romoscanu
10,398,500 B2 9/2019 Huszar et al.
10,441,192 B2 10/2019 Thompson et al.
10,443,929 B2 10/2019 Janeke
10,448,859 B2 10/2019 Wehner et al.
10,463,303 B2 11/2019 Donnay et al.
10,470,682 B2 11/2019 Deno et al.
10,478,247 B2 11/2019 Litscher et al.
10,478,325 B2 11/2019 Syed
10,492,729 B2 12/2019 de la Rama et al.
10,492,869 B2 12/2019 Malinin et al.
10,499,826 B2 12/2019 Balachandran et al.
10,506,938 B2 12/2019 Wu et al.
10,512,419 B2 12/2019 Craven et al.
10,537,259 B2 1/2020 Wu et al.
10,542,899 B2 1/2020 Wu et al.
10,556,091 B2 2/2020 Truhler et al.
10,575,742 B2 3/2020 Wu et al.
10,575,745 B2 3/2020 Solis
10,578,737 B2 3/2020 Gliner et al.
10,595,738 B2 3/2020 Sterrett et al.
10,595,740 B2 3/2020 Hoitink et al.
10,602,948 B2 3/2020 Wu et al.
10,646,692 B2 5/2020 Tegg et al.
10,653,423 B2 5/2020 Starnes
10,675,086 B2 6/2020 Afonso et al.
10,702,177 B2 7/2020 Aujla
10,702,677 B2 7/2020 Okamura et al.
10,729,500 B2 8/2020 Quinn et al.
10,737,060 B2 8/2020 Gupta et al.
10,750,975 B2 8/2020 Hill et al.
10,799,148 B2 10/2020 Mosesov et al.
10,799,188 B2 10/2020 Erdemir et al.
10,813,590 B2 10/2020 Ruppersberg
10,835,712 B2 11/2020 Wada
10,842,990 B2 11/2020 de la Rama et al.
10,857,349 B2 12/2020 de la Rama et al.
10,869,992 B2 12/2020 Pai et al.
10,898,104 B2 1/2021 Olson et al.
10,898,685 B2 1/2021 Tegg
10,905,347 B2 2/2021 Fuentes-Ortega et al.
10,912,925 B2 2/2021 Houck
10,932,685 B2 3/2021 Wu
10,945,626 B2 3/2021 Fuentes-Ortega et al.
10,946,167 B2 3/2021 Mintz et al.
10,953,196 B2 3/2021 Raab et al.
10,959,636 B2 3/2021 Dahlen et al.
10,966,623 B2 4/2021 Wu et al.
10,966,753 B2 4/2021 Coyle et al.
10,967,150 B2 4/2021 Helgeson et al.
10,973,427 B2 4/2021 Aujla
10,987,045 B2 4/2021 Basu et al.
11,033,715 B2 6/2021 Beeckler et al.
11,039,772 B2 6/2021 Wu et al.
11,039,773 B2 6/2021 Sterrett et al.
11,077,298 B2 8/2021 Waldhauser et al.
11,083,400 B2 8/2021 Hoitink et al.
11,116,436 B2 9/2021 Wu et al.
11,116,476 B2 9/2021 Buesseler et al.
11,116,942 B2 9/2021 Beeckler et al.
11,123,051 B2 9/2021 Van Der Linde et al.
11,141,568 B2 10/2021 Hsueh et al.
11,160,482 B2 11/2021 Solis
11,172,858 B2 11/2021 Olson et al.
11,205,300 B2 12/2021 Carbonera et al.
D940,310 S 1/2022 de la Rama et al.
11,272,886 B2 3/2022 Harlev et al.
D951,438 S 5/2022 de la Rama et al.
D952,140 S 5/2022 de la Rama et al.
D952,843 S 5/2022 de la Rama et al.
11,382,690 B2 7/2022 Smith et al.
11,382,743 B2 7/2022 Marchand et al.
11,383,078 B2 7/2022 de la Rama et al.
11,406,312 B2 8/2022 Deno et al.
11,419,673 B2 8/2022 Kauphusman et al.
11,426,111 B2 8/2022 Olson
11,433,220 B2 9/2022 Oliverius et al.
11,439,460 B2 9/2022 Sliwa et al.
11,446,470 B2 9/2022 Castelli et al.
11,446,471 B2 9/2022 Grunewald
D966,506 S 10/2022 de la Rama et al.
D966,507 S 10/2022 de la Rama et al.
11,478,299 B2 10/2022 Webster et al.
11,484,690 B2 11/2022 Tegg et al.
11,491,311 B2 11/2022 Selkee
11,504,205 B2 11/2022 Brucker et al.
11,511,078 B2 11/2022 Gonzalez
11,517,715 B2 12/2022 Govari
11,517,716 B2 12/2022 Nguyen et al.
11,523,748 B2 12/2022 Esguerra Wilczynski et al.
11,540,876 B2 1/2023 Oliverius et al.
11,540,878 B2 1/2023 Fuentes-Ortega et al.
11,547,437 B2 1/2023 Zarembinski
11,553,962 B2 1/2023 Harlev et al.
11,559,663 B2 1/2023 Hannon et al.
11,583,334 B2 2/2023 Caples et al.
11,583,658 B2 2/2023 Yang et al.
11,602,630 B2 3/2023 Vetter et al.
11,617,616 B2 4/2023 Clark et al.
11,617,859 B2 4/2023 Hsueh et al.
11,617,861 B2 4/2023 Pai et al.
11,622,806 B2 4/2023 Romoscanu
11,628,009 B2 4/2023 Aujla
11,660,119 B2 5/2023 Hassett
11,672,947 B2 6/2023 Tegg et al.
11,684,473 B2 6/2023 Righini et al.
11,690,552 B2 7/2023 Wu et al.
11,723,574 B2 8/2023 Wu et al.
11,771,373 B2 10/2023 Nakar et al.
11,779,770 B2 10/2023 Botzer
11,786,301 B2 10/2023 Olson
11,806,152 B2 11/2023 Zeidan et al.
11,813,410 B2 11/2023 Olson et al.
11,832,965 B2 12/2023 Wang
11,850,051 B2 12/2023 Selkee et al.
11,857,250 B2 1/2024 Corvi et al.
11,896,819 B2 2/2024 Rosa et al.
11,904,109 B2 2/2024 Gliner et al.
11,938,316 B2 3/2024 Feler et al.
11,950,827 B2 4/2024 Rafiee et al.
11,950,840 B2 4/2024 Govari et al.
11,950,841 B2 4/2024 Govari et al.
11,950,897 B2 4/2024 Esguerra Wilczynski et al.
11,950,930 B2 4/2024 Gliner et al.
11,957,847 B2 4/2024 Houck
11,992,321 B2 5/2024 Solis
12,004,804 B2 6/2024 Govari et al.
12,004,805 B2 6/2024 Schuler et al.
12,011,216 B2 6/2024 Zirkle et al.
12,036,027 B2 7/2024 Olson et al.
12,036,371 B2 7/2024 Hsueh et al.
12,064,168 B2 8/2024 Harlev et al.
12,076,079 B2 9/2024 Oliverius et al.
12,083,288 B2 9/2024 Lopez et al.
12,089,940 B2 9/2024 Hoitink et al.
12,097,034 B2 9/2024 Wu et al.
12,102,382 B2 10/2024 Govari et al.
12,109,031 B2 10/2024 Deno et al.
12,109,373 B2 10/2024 Srivastava et al.
12,114,922 B2 10/2024 Harlev et al.
12,121,357 B2 10/2024 de la Rama et al.
12,121,438 B2 10/2024 Dehdashtian et al.
12,138,404 B2 11/2024 Beeckler et al.
12,144,629 B2 11/2024 Wu et al.
12,171,488 B2 12/2024 Narayan et al.
12,178,500 B2 12/2024 Highsmith
12,185,961 B2 1/2025 Nguyen et al.
12,186,010 B2 1/2025 Govari et al.
12,193,728 B2 1/2025 Narayan

(56) References Cited

U.S. PATENT DOCUMENTS 12,193,823 B2 1/2025 Wu et al.
12,194,251 B2 1/2025 Tavallaei et al.
12,201,351 B2 1/2025 Kim et al.
12,201,421 B2 1/2025 Garai et al.
12,207,795 B2 1/2025 Purohit et al.
12,214,206 B2 2/2025 Ward et al.
12,220,541 B2 2/2025 Highsmith et al.
12,221,163 B2 2/2025 Günther et al.
12,226,141 B2 2/2025 Yaffe et al.
12,226,314 B2 2/2025 Reimer et al.
12,232,755 B2 2/2025 Phan et al.
12,232,874 B2 2/2025 Salazar et al.
12,232,908 B2 2/2025 Stigall et al.
12,239,364 B2 3/2025 Govari et al.
12,246,143 B2 3/2025 Leeflang et al.
12,251,224 B2 3/2025 Selkee et al.
12,256,913 B2 3/2025 Nunan
12,256,984 B2 3/2025 Ku et al.
12,256,985 B2 3/2025 Zhou et al.
12,263,014 B2 4/2025 Tegg et al.
12,263,338 B2 4/2025 de la Rama et al.
12,268,456 B2 4/2025 Harlev et al.
12,290,646 B2 5/2025 Osypka et al.
12,310,715 B2 5/2025 Hoitink et al.
D1,078,039 S 6/2025 Tegg et al.
12,324,620 B2 6/2025 de la Rama et al.
12,337,124 B2 6/2025 Campbell et al.
2002/0165484 A1 11/2002 Bowe et al.
2005/0159741 A1 7/2005 Paul et al.
2009/0198300 A1 8/2009 Zhang et al.
2011/0066029 A1* 3/2011 Lyu .................. A61M 25/0133 600/424
2011/0118726 A1 5/2011 de la Rama et al.
2012/0271302 A1 10/2012 Behl et al.
2012/0296232 A1 11/2012 Ng
2013/0253504 A1 9/2013 Fang
2013/0274582 A1 10/2013 Afonso et al.
2014/0035578 A1* 2/2014 Song ........................ G01V 3/32 324/309
2014/0100639 A1 4/2014 Lee et al.
2014/0107835 A1* 4/2014 Biasi .................... B67D 1/0892 700/231
2014/0200639 A1 7/2014 de la Rama
2014/0269602 A1 9/2014 Kawagishi
2014/0276226 A1 9/2014 Meller et al.
2014/0296846 A1 10/2014 Huszar et al.
2014/0296902 A1 10/2014 Huszar et al.
2014/0316496 A1 10/2014 Masson et al.
2014/0336636 A1 11/2014 Huszar et al.
2014/0350564 A1 11/2014 Huszar et al.
2015/0001191 A1 1/2015 Lee et al.
2015/0011991 A1 1/2015 Buysman et al.
2015/0105645 A1 4/2015 Subramaniam et al.
2015/0119911 A1 4/2015 Mckenzie
2015/0141785 A1 5/2015 Hayam et al.
2015/0159741 A1 6/2015 Versteyhe et al.
2015/0351652 A1 12/2015 Marecki et al.
2016/0143588 A1 5/2016 Hoitink et al.
2016/0213423 A1 7/2016 Kauphusman et al.
2016/0213916 A1 7/2016 de la Rama
2016/0278851 A1 9/2016 Mannion et al.
2016/0317094 A1 11/2016 Byrd et al.
2016/0331471 A1 11/2016 Deno et al.
2016/0331933 A1 11/2016 Knutsen
2016/0374582 A1 12/2016 Wu et al.
2016/0374753 A1 12/2016 Wu et al.
2017/0000365 A1 1/2017 Wu et al.
2017/0042449 A1 2/2017 Deno et al.
2017/0049348 A1 2/2017 Deno et al.
2017/0112404 A1 4/2017 de la Rama et al.
2017/0112405 A1 4/2017 Sterrett et al.
2017/0273738 A1 9/2017 Wu
2017/0319269 A1 11/2017 Oliverius et al.
2017/0367756 A1 12/2017 Sliwa et al.
2018/0042667 A1 2/2018 Pappone et al.
2018/0056038 A1 3/2018 Aujla
2018/0070845 A1 3/2018 Hoitink et al.
2018/0085064 A1 3/2018 Auerbach et al.
2018/0116539 A1 5/2018 Olson et al.
2018/0161093 A1 6/2018 Basu et al.
2018/0193089 A1 7/2018 Wu
2018/0229030 A1 8/2018 Dubuclet et al.
2018/0235496 A1 8/2018 Wu et al.
2018/0297936 A1* 10/2018 Imig .................... C07C 233/66
2018/0303361 A1 10/2018 Wu et al.
2018/0335519 A1 11/2018 Gliner et al.
2018/0369574 A1 12/2018 Dubuclet et al.
2019/0009052 A1 1/2019 Oliverius et al.
2019/0125378 A1 5/2019 Shelton, IV et al.
2019/0175043 A1 6/2019 Wu et al.
2019/0192826 A1 6/2019 Wada
2019/0239812 A1 8/2019 Botzer et al.
2020/0000359 A1 1/2020 de la Rama et al.
2020/0054391 A1 2/2020 Litscher et al.
2020/0069365 A1 3/2020 Harlev et al.
2020/0077908 A1 3/2020 Hagfors et al.
2020/0077912 A1 3/2020 Wu et al.
2020/0113469 A1 4/2020 Sahadevan et al.
2020/0121894 A1 4/2020 Prabhu et al.
2020/0138378 A1 5/2020 de la Rama et al.
2020/0155021 A1 5/2020 Wu et al.
2020/0205737 A1 7/2020 Beeckler
2020/0214635 A1 7/2020 Dahlen et al.
2020/0221966 A1 7/2020 Wu et al.
2020/0229727 A1 7/2020 Hoitink et al.
2020/0229866 A1 7/2020 Harlev et al.
2020/0253496 A1 8/2020 Deno et al.
2020/0305744 A1 10/2020 Weerakoon et al.
2020/0329989 A1 10/2020 Aujla
2020/0345262 A1 11/2020 Selkee et al.
2020/0360657 A1 11/2020 Ganske
2020/0398026 A1 12/2020 Castelli et al.
2020/0405166 A1 12/2020 Wu et al.
2021/0015551 A1 1/2021 Fuentes-Ortega et al.
2021/0038860 A1 2/2021 Mintz et al.
2021/0059745 A1 3/2021 Highsmith
2021/0068693 A1 3/2021 Fuentes-Ortega et al.
2021/0077183 A1 3/2021 Basu et al.
2021/0085920 A1 3/2021 Roberts et al.
2021/0085921 A1 3/2021 Roberts et al.
2021/0121231 A1 4/2021 Basu et al.
2021/0145342 A1 5/2021 Wang
2021/0153932 A1 5/2021 Voth et al.
2021/0187246 A1 6/2021 Houck
2021/0204871 A1 7/2021 Goedeke et al.
2021/0228136 A1 7/2021 Fuentes-Ortega et al.
2021/0228137 A1 7/2021 Aujla
2021/0267693 A1 9/2021 Deno et al.
2021/0268234 A1 9/2021 Helgeson et al.
2021/0298656 A1 9/2021 Wu et al.
2021/0361216 A1 11/2021 Hoitink et al.
2021/0361428 A1 11/2021 Dixon
2021/0369132 A1 12/2021 Van Niekerk et al.
2021/0369338 A1 12/2021 Govari et al.
2021/0369339 A1 12/2021 Salazar et al.
2021/0370022 A1 12/2021 Bean et al.
2021/0401345 A1 12/2021 Wu et al.
2021/0402148 A1 12/2021 Beeckler et al.
2022/0023594 A1 1/2022 Pai
2022/0054066 A1 2/2022 Solis
2022/0054198 A1 2/2022 Tegg et al.
2022/0061727 A1 3/2022 Olson et al.
2022/0071704 A1 3/2022 Le
2022/0079496 A1 3/2022 Squires et al.
2022/0110675 A1 4/2022 Govari et al.
2022/0126063 A1 4/2022 Weber
2022/0175445 A1 6/2022 Sutermeister et al.
2022/0225941 A1 7/2022 Smaill et al.
2022/0265345 A1 8/2022 Gottsche et al.
2022/0273913 A1 9/2022 Worley et al.
2022/0313353 A1 10/2022 Palushi et al.
2022/0313961 A1 10/2022 Tang
2022/0331553 A1 10/2022 Strom et al.
2022/0354568 A1 11/2022 Pappone et al.

(56) References Cited

U.S. PATENT DOCUMENTS

| | | | |
|---|---|---|---|
| 2022/0361942 | A1 | 11/2022 | Lichter et al. |
| 2022/0370119 | A1 | 11/2022 | Govari et al. |
| 2022/0370121 | A1 | 11/2022 | Highsmith |
| 2022/0370122 | A1 | 11/2022 | Smail |
| 2022/0370792 | A1 | 11/2022 | de la Rama et al. |
| 2022/0387012 | A1 | 12/2022 | Nunan |
| 2022/0387099 | A1 | 12/2022 | Cohen et al. |
| 2022/0387100 | A1 | 12/2022 | Greenbaum et al. |
| 2022/0395214 | A1 | 12/2022 | Altman et al. |
| 2022/0401032 | A1 | 12/2022 | Govari et al. |
| 2022/0401693 | A1 | 12/2022 | Oliverius et al. |
| 2022/0409860 | A1 | 12/2022 | Castelli et al. |
| 2023/0000415 | A1 | 1/2023 | Olson |
| 2023/0000547 | A1 | 1/2023 | Viswanathan et al. |
| 2023/0000548 | A1 | 1/2023 | Viswanathan |
| 2023/0000550 | A1 | 1/2023 | Nedved et al. |
| 2023/0001148 | A1 | 1/2023 | Sharma |
| 2023/0008044 | A1 | 1/2023 | Rao et al. |
| 2023/0009573 | A1 | 1/2023 | Van Niekerk et al. |
| 2023/0011509 | A1 | 1/2023 | Sterrett et al. |
| 2023/0012307 | A1 | 1/2023 | Harlev et al. |
| 2023/0024690 | A1 | 1/2023 | Cohen et al. |
| 2023/0028549 | A1 | 1/2023 | Maierhofer et al. |
| 2023/0029648 | A1 | 2/2023 | Van Niekerk et al. |
| 2023/0033444 | A1 | 2/2023 | Knighton et al. |
| 2023/0035917 | A1 | 2/2023 | Gutbrod et al. |
| 2023/0043627 | A1 | 2/2023 | Tang et al. |
| 2023/0043978 | A1 | 2/2023 | Govari |
| 2023/0046955 | A1 | 2/2023 | Akagane |
| 2023/0049942 | A1 | 2/2023 | Narayan et al. |
| 2023/0052130 | A1 | 2/2023 | Govari et al. |
| 2023/0053064 | A1 | 2/2023 | Altmann |
| 2023/0055089 | A1 | 2/2023 | Govari et al. |
| 2023/0064082 | A1 | 3/2023 | Sun et al. |
| 2023/0078216 | A1 | 3/2023 | Govari |
| 2023/0083615 | A1 | 3/2023 | Nguyen et al. |
| 2023/0084626 | A1 | 3/2023 | Grunewald |
| 2023/0105390 | A1 | 4/2023 | Gutbrod et al. |
| 2023/0105973 | A1 | 4/2023 | Gutbrod et al. |
| 2023/0114222 | A1 | 4/2023 | Esguerra Wilczynski et al. |
| 2023/0121397 | A1 | 4/2023 | Oliverius et al. |
| 2023/0123266 | A1 | 4/2023 | Castelli et al. |
| 2023/0149069 | A1 | 5/2023 | Van Niekerk et al. |
| 2023/0149070 | A1 | 5/2023 | Olson et al. |
| 2023/0149675 | A1 | 5/2023 | Leung et al. |
| 2023/0172611 | A1 | 6/2023 | Biscarrat et al. |
| 2023/0172659 | A1 | 6/2023 | Olson et al. |
| 2023/0172661 | A1 | 6/2023 | Harlev et al. |
| 2023/0190166 | A1 | 6/2023 | Spector |
| 2023/0190198 | A1 | 6/2023 | Pederson et al. |
| 2023/0190369 | A1 | 6/2023 | Caples et al. |
| 2023/0200894 | A1 | 6/2023 | Rodriguez et al. |
| 2023/0200895 | A1 | 6/2023 | Ebrahimi et al. |
| 2023/0210433 | A1 | 7/2023 | Abbas et al. |
| 2023/0264031 | A1 | 8/2023 | Harlev et al. |
| 2023/0284956 | A1 | 9/2023 | Wu et al. |
| 2023/0310071 | A1 | 10/2023 | Van Niekerk et al. |
| 2023/0329618 | A1 | 10/2023 | Wu et al. |
| 2023/0329784 | A1 | 10/2023 | Stewart et al. |
| 2023/0404657 | A1 | 12/2023 | Olson |
| 2023/0405338 | A1 | 12/2023 | Botzer |
| 2023/0414156 | A1 | 12/2023 | Liu et al. |
| 2024/0008920 | A1 | 1/2024 | Govari et al. |
| 2024/0033470 | A1 | 2/2024 | Olson et al. |
| 2024/0057939 | A1 | 2/2024 | Wang |
| 2024/0081712 | A1 | 3/2024 | Selkee et al. |
| 2024/0081905 | A1 | 3/2024 | Corvi et al. |
| 2024/0123191 | A1 | 4/2024 | Highsmith et al. |
| 2024/0173070 | A1 | 5/2024 | Selkee et al. |
| 2024/0198054 | A1 | 6/2024 | Schultz |
| 2024/0206966 | A1 | 6/2024 | Kelly et al. |
| 2024/0207578 | A1 | 6/2024 | Soltis et al. |
| 2024/0225726 | A1 | 7/2024 | Govari et al. |
| 2024/0245360 | A1 | 7/2024 | Gliner et al. |
| 2024/0252815 | A1 | 8/2024 | de la Rama et al. |
| 2024/0277277 | A1 | 8/2024 | Hoitink et al. |
| 2024/0306900 | A1 | 9/2024 | Thissen et al. |
| 2024/0325691 | A1 | 10/2024 | Bogusky |
| 2024/0350063 | A1 | 10/2024 | Olson et al. |
| 2024/0350070 | A1 | 10/2024 | Rodriguez |
| 2024/0366299 | A1 | 11/2024 | Dando et al. |
| 2024/0366301 | A1 | 11/2024 | Govari et al. |
| 2024/0415438 | A1 | 12/2024 | Wu et al. |
| 2024/0423707 | A1 | 12/2024 | Govari et al. |
| 2025/0009272 | A1 | 1/2025 | de la Rama et al. |
| 2025/0017648 | A1 | 1/2025 | Kim |
| 2025/0025231 | A1 | 1/2025 | Oliverius et al. |
| 2025/0025643 | A1 | 1/2025 | Sigmon, Jr. et al. |
| 2025/0032028 | A1 | 1/2025 | Deno et al. |
| 2025/0032181 | A1 | 1/2025 | Harlev et al. |
| 2025/0032749 | A1 | 1/2025 | Tao et al. |
| 2025/0040853 | A1 | 2/2025 | Wu et al. |
| 2025/0040889 | A1 | 2/2025 | Smaill et al. |
| 2025/0040955 | A1 | 2/2025 | Murray et al. |
| 2025/0043590 | A1 | 2/2025 | Furseth et al. |
| 2025/0049460 | A1 | 2/2025 | Worrell et al. |
| 2025/0057595 | A1 | 2/2025 | Narayan et al. |
| 2025/0064430 | A1 | 2/2025 | Mantri et al. |
| 2025/0064585 | A1 | 2/2025 | Vidlund et al. |
| 2025/0072897 | A1 | 3/2025 | Reu et al. |
| 2025/0082438 | A1 | 3/2025 | Seeralan et al. |
| 2025/0082901 | A1 | 3/2025 | Govari et al. |
| 2025/0082903 | A1 | 3/2025 | Hsueh et al. |
| 2025/0090070 | A1 | 3/2025 | Wu et al. |
| 2025/0090151 | A1 | 3/2025 | Pedersen et al. |
| 2025/0090225 | A1 | 3/2025 | Savastano et al. |
| 2025/0090807 | A1 | 3/2025 | Padilla et al. |
| 2025/0099176 | A1 | 3/2025 | Kim et al. |
| 2025/0127567 | A1 | 4/2025 | Highsmith |
| 2025/0152104 | A1 | 5/2025 | Tegg et al. |
| 2025/0152932 | A1 | 5/2025 | de la Rama et al. |
| 2025/0160942 | A1 | 5/2025 | Ku et al. |
| 2025/0177037 | A1 | 6/2025 | Olson et al. |
| 2025/0185968 | A1 | 6/2025 | Salazar et al. |
| 2025/0185969 | A1 | 6/2025 | Selkee et al. |

FOREIGN PATENT DOCUMENTS

| | | | |
|---|---|---|---|
| AU | 2016204353 | A1 | 1/2017 |
| AU | 2016204355 | A1 | 1/2017 |
| CA | 2934209 | A1 | 12/2016 |
| CA | 2934211 | A1 | 12/2016 |
| CA | 2934214 | A1 | 12/2016 |
| CN | 101797181 | A | 8/2010 |
| CN | 101927053 | B | 1/2015 |
| CN | 103157168 | B | 4/2015 |
| CN | 105960201 | A | 9/2016 |
| CN | 106859765 | A | 6/2017 |
| CN | 106901831 | A | 6/2017 |
| CN | 206880930 | U | 1/2018 |
| CN | 104958824 | B | 12/2018 |
| CN | 104434083 | B | 4/2019 |
| CN | 104968261 | B | 5/2019 |
| CN | 105592778 | B | 7/2019 |
| CN | 105960200 | B | 8/2019 |
| CN | 105451680 | B | 10/2019 |
| CN | 110536646 | A | 12/2019 |
| CN | 110604860 | A | 12/2019 |
| CN | 105960201 | B | 3/2020 |
| CN | 111225627 | A | 6/2020 |
| CN | 111227929 | A | 6/2020 |
| CN | 111374755 | A | 7/2020 |
| CN | 111432739 | A | 7/2020 |
| CN | 111657866 | A | 9/2020 |
| CN | 111839499 | A | 10/2020 |
| CN | 106264715 | B | 11/2020 |
| CN | 106264716 | B | 11/2020 |
| CN | 112040861 | A | 12/2020 |
| CN | 106308790 | B | 6/2021 |
| CN | 107529958 | B | 7/2021 |
| CN | 109310469 | B | 7/2021 |
| CN | 213665310 | U | 7/2021 |
| CN | 213821695 | U | 7/2021 |
| CN | 109641121 | B | 9/2021 |

(56) References Cited

FOREIGN PATENT DOCUMENTS

| | | | |
|---|---|---|---|
| CN | 109952123 | B | 9/2021 |
| CN | 110545874 | B | 9/2021 |
| CN | 110559544 | B | 9/2021 |
| CN | 113425304 | A | 9/2021 |
| CN | 105615994 | B | 10/2021 |
| CN | 109963610 | B | 11/2021 |
| CN | 113939327 | A | 1/2022 |
| CN | 108289709 | B | 3/2022 |
| CN | 114126522 | A | 3/2022 |
| CN | 114343831 | A | 4/2022 |
| CN | 114375211 | A | 4/2022 |
| CN | 216257368 | U | 4/2022 |
| CN | 114424971 | A | 5/2022 |
| CN | 111246907 | B | 7/2022 |
| CN | 114727815 | A | 7/2022 |
| CN | 114828745 | A | 7/2022 |
| CN | 107773300 | B | 8/2022 |
| CN | 108567424 | B | 8/2022 |
| CN | 114903491 | A | 8/2022 |
| CN | 106859638 | B | 10/2022 |
| CN | 108283520 | B | 10/2022 |
| CN | 110547865 | B | 10/2022 |
| CN | 115137944 | A | 10/2022 |
| CN | 107343816 | B | 11/2022 |
| CN | 113545841 | B | 11/2022 |
| CN | 115281680 | A | 11/2022 |
| CN | 115363746 | A | 11/2022 |
| CN | 115364333 | A | 11/2022 |
| CN | 115379873 | A | 11/2022 |
| CN | 217793303 | U | 11/2022 |
| CN | 115426941 | A | 12/2022 |
| CN | 115444544 | A | 12/2022 |
| CN | 115444549 | A | 12/2022 |
| CN | 115461007 | A | 12/2022 |
| CN | 115500932 | A | 12/2022 |
| CN | 115500933 | A | 12/2022 |
| CN | 115590606 | A | 1/2023 |
| CN | 115590608 | A | 1/2023 |
| CN | 115666700 | A | 1/2023 |
| CN | 107343784 | B | 2/2023 |
| CN | 115697221 | A | 2/2023 |
| CN | 115702823 | A | 2/2023 |
| CN | 115768346 | A | 3/2023 |
| CN | 115886978 | A | 4/2023 |
| CN | 115942915 | A | 4/2023 |
| CN | 115990309 | A | 4/2023 |
| CN | 110520067 | B | 5/2023 |
| CN | 111225627 | B | 5/2023 |
| CN | 116115323 | A | 5/2023 |
| CN | 116135163 | A | 5/2023 |
| CN | 116137804 | A | 5/2023 |
| CN | 116157084 | A | 5/2023 |
| CN | 116157174 | A | 5/2023 |
| CN | 116158839 | A | 5/2023 |
| CN | 106419897 | B | 6/2023 |
| CN | 111065350 | B | 6/2023 |
| CN | 116234511 | A | 6/2023 |
| CN | 116250914 | A | 6/2023 |
| CN | 116327346 | A | 6/2023 |
| CN | 109259854 | B | 10/2023 |
| CN | 111657866 | B | 10/2023 |
| CN | 117355271 | A | 1/2024 |
| CN | 117396150 | A | 1/2024 |
| CN | 114209331 | B | 2/2024 |
| CN | 117597080 | A | 2/2024 |
| CN | 111836579 | B | 3/2024 |
| CN | 112704546 | B | 3/2024 |
| CN | 117942483 | A | 4/2024 |
| CN | 117958829 | A | 5/2024 |
| CN | 115379873 | B | 6/2024 |
| CN | 118234442 | A | 6/2024 |
| CN | 118251185 | A | 6/2024 |
| CN | 111096749 | B | 7/2024 |
| CN | 113164127 | B | 7/2024 |
| CN | 118384409 | A | 7/2024 |
| CN | 113993572 | B | 8/2024 |
| CN | 114040724 | B | 8/2024 |
| CN | 111683581 | B | 9/2024 |
| CN | 112040861 | B | 9/2024 |
| CN | 118697365 | A | 9/2024 |
| CN | 118715039 | A | 9/2024 |
| CN | 111683614 | B | 10/2024 |
| CN | 112121284 | B | 11/2024 |
| CN | 118891015 | A | 11/2024 |
| CN | 118900667 | A | 11/2024 |
| CN | 113226443 | B | 12/2024 |
| CN | 111374755 | B | 1/2025 |
| CN | 111436928 | B | 1/2025 |
| CN | 111918606 | B | 1/2025 |
| CN | 112969498 | B | 1/2025 |
| CN | 113543728 | B | 1/2025 |
| CN | 113693716 | B | 1/2025 |
| CN | 114340535 | B | 1/2025 |
| CN | 115284943 | B | 1/2025 |
| CN | 115338627 | B | 1/2025 |
| CN | 111691972 | B | 2/2025 |
| CN | 112278762 | B | 2/2025 |
| CN | 112520267 | B | 2/2025 |
| CN | 112674068 | B | 2/2025 |
| CN | 119385661 | A | 2/2025 |
| CN | 119455229 | A | 2/2025 |
| CN | 111462635 | B | 3/2025 |
| CN | 111994108 | B | 3/2025 |
| CN | 112207374 | B | 3/2025 |
| CN | 119607406 | A | 3/2025 |
| CN | 112040860 | B | 5/2025 |
| CN | 114423344 | B | 5/2025 |
| CN | 111374756 | B | 6/2025 |
| CN | 112135576 | B | 6/2025 |
| CN | 115461007 | B | 6/2025 |
| EP | 0889744 | B1 | 1/2004 |
| EP | 1254641 | B1 | 11/2008 |
| EP | 1690564 | B1 | 4/2009 |
| EP | 1723981 | B1 | 8/2010 |
| EP | 2135634 | B1 | 10/2011 |
| EP | 2018203 | B1 | 6/2012 |
| EP | 1814450 | B1 | 1/2013 |
| EP | 2269532 | B1 | 3/2013 |
| EP | 2664295 | A1 | 11/2013 |
| EP | 2604306 | B1 | 1/2014 |
| EP | 2732843 | A1 | 5/2014 |
| EP | 2747680 | A2 | 7/2014 |
| EP | 2752153 | A1 | 7/2014 |
| EP | 2907462 | A1 | 8/2015 |
| EP | 2915555 | A1 | 9/2015 |
| EP | 1968679 | B1 | 9/2016 |
| EP | 2241279 | B1 | 9/2016 |
| EP | 3111871 | A1 | 1/2017 |
| EP | 3111872 | A1 | 1/2017 |
| EP | 2796103 | B1 | 2/2017 |
| EP | 3222209 | A1 | 9/2017 |
| EP | 2792322 | B1 | 10/2017 |
| EP | 2792323 | B1 | 10/2017 |
| EP | 3115076 | A4 | 10/2017 |
| EP | 3117863 | A4 | 10/2017 |
| EP | 3030182 | B1 | 1/2018 |
| EP | 3287092 | A1 | 2/2018 |
| EP | 3111871 | B1 | 3/2018 |
| EP | 3111872 | B1 | 4/2018 |
| EP | 3057488 | B1 | 5/2018 |
| EP | 2848226 | B1 | 7/2018 |
| EP | 3345540 | A1 | 7/2018 |
| EP | 3363397 | A1 | 8/2018 |
| EP | 3391928 | A1 | 10/2018 |
| EP | 3122276 | B1 | 11/2018 |
| EP | 3398549 | A1 | 11/2018 |
| EP | 3403571 | A1 | 11/2018 |
| EP | 1759668 | B1 | 12/2018 |
| EP | 3020352 | B1 | 12/2018 |
| EP | 3037122 | B1 | 12/2018 |
| EP | 2234537 | B1 | 1/2019 |
| EP | 2569040 | B1 | 2/2019 |
| EP | 3023052 | B1 | 3/2019 |
| EP | 3073908 | B1 | 4/2019 |

(56) References Cited

FOREIGN PATENT DOCUMENTS

EP 3466363 A1 4/2019
EP 2550989 B1 6/2019
EP 3512589 A1 7/2019
EP 3512590 A1 7/2019
EP 3527125 A1 8/2019
EP 3531903 A1 9/2019
EP 3581229 A1 12/2019
EP 3434218 B1 2/2020
EP 2908723 B1 3/2020
EP 3335658 B1 4/2020
EP 3073907 B1 6/2020
EP 3673851 A1 7/2020
EP 3114987 B1 8/2020
EP 3178516 B1 9/2020
EP 3708104 A1 9/2020
EP 3711662 A1 9/2020
EP 3721796 A1 10/2020
EP 3733103 A1 11/2020
EP 3738508 A1 11/2020
EP 3738509 A1 11/2020
EP 3340916 B1 12/2020
EP 3579908 B1 12/2020
EP 3749174 A1 12/2020
EP 3749191 A1 12/2020
EP 3749192 A1 12/2020
EP 3749195 A1 12/2020
EP 3750475 A1 12/2020
EP 3768185 A1 1/2021
EP 2155301 B1 4/2021
EP 3432820 B1 4/2021
EP 3476331 B1 5/2021
EP 3579758 B1 5/2021
EP 2809254 B1 6/2021
EP 3508245 B1 7/2021
EP 3858277 A1 8/2021
EP 3892221 A1 10/2021
EP 3902461 A1 11/2021
EP 3915477 A1 12/2021
EP 3915501 A1 12/2021
EP 3919014 A1 12/2021
EP 3932343 A4 1/2022
EP 3791820 B9 4/2022
EP 3986520 A1 4/2022
EP 3991680 A2 5/2022
EP 3995079 A1 5/2022
EP 4000506 A1 5/2022
EP 3860447 A4 7/2022
EP 4025112 A1 7/2022
EP 4031007 A1 7/2022
EP 4031044 A2 7/2022
EP 4039215 A1 8/2022
EP 4041112 A1 8/2022
EP 3363397 B1 9/2022
EP 3673944 B1 9/2022
EP 3915501 B1 9/2022
EP 3949848 A4 9/2022
EP 4076193 A1 10/2022
EP 4078255 A1 10/2022
EP 4079365 A2 10/2022
EP 3609414 B1 11/2022
EP 4088676 A1 11/2022
EP 4091565 A1 11/2022
EP 4091569 A1 11/2022
EP 4093274 A1 11/2022
EP 4096545 A1 12/2022
EP 4101372 A1 12/2022
EP 4101375 A1 12/2022
EP 4101383 A1 12/2022
EP 4104763 A1 12/2022
EP 4106625 A1 12/2022
EP 4106853 A2 12/2022
EP 2844193 B1 1/2023
EP 3100696 B1 1/2023
EP 3166524 B1 1/2023
EP 3946123 A4 1/2023
EP 4079365 A3 1/2023
EP 4115832 A1 1/2023
EP 4115833 A1 1/2023
EP 4115936 A1 1/2023
EP 4120963 A1 1/2023
EP 4122414 A1 1/2023
EP 4134032 A1 2/2023
EP 4137080 A1 2/2023
EP 3115076 B1 3/2023
EP 3658054 B1 3/2023
EP 4144397 A1 3/2023
EP 4157420 A1 4/2023
EP 4159124 A1 4/2023
EP 4164519 A1 4/2023
EP 4167886 A1 4/2023
EP 4179991 A1 5/2023
EP 4181810 A1 5/2023
EP 4185224 A1 5/2023
EP 4185225 A1 5/2023
EP 2803329 B1 6/2023
EP 3015064 B1 6/2023
EP 3141183 B1 6/2023
EP 3398549 B1 6/2023
EP 3768185 B1 6/2023
EP 4190232 A1 6/2023
EP 4190257 A2 6/2023
EP 4193947 A1 6/2023
EP 4201356 A2 6/2023
EP 4201357 A1 6/2023
EP 4205684 A1 7/2023
EP 4218579 A1 8/2023
EP 2816966 B1 10/2023
EP 3113671 B1 10/2023
EP 3681427 B1 10/2023
EP 3738509 B1 10/2023
EP 3749195 B1 10/2023
EP 4257068 A1 10/2023
EP 3209234 B1 11/2023
EP 3527125 B1 11/2023
EP 3721796 B1 11/2023
EP 3731747 B1 11/2023
EP 3998935 B1 11/2023
EP 4091547 B1 11/2023
EP 4233699 A3 11/2023
EP 4272631 A2 11/2023
EP 4291123 A1 12/2023
EP 3192442 B1 1/2024
EP 3892221 B1 1/2024
EP 4298995 A2 1/2024
EP 3738508 B1 2/2024
EP 4137051 B1 3/2024
EP 4340762 A1 3/2024
EP 3124069 B1 4/2024
EP 4003234 B9 4/2024
EP 4159124 B1 4/2024
EP 3943139 B1 5/2024
EP 4167886 B1 5/2024
EP 4353171 A3 5/2024
EP 4360572 A1 5/2024
EP 4362831 A1 5/2024
EP 4364680 A2 5/2024
EP 4364765 A2 5/2024
EP 4370064 A1 5/2024
EP 3498156 B1 6/2024
EP 4044947 B1 6/2024
EP 4344722 A3 6/2024
EP 4376745 A1 6/2024
EP 4378515 A2 6/2024
EP 3573559 B1 7/2024
EP 3673851 7/2024
EP 3834728 7/2024
EP 4181810 A4 7/2024
EP 4272631 A3 7/2024
EP 4364680 A3 7/2024
EP 4392113 A1 7/2024
EP 3603493 B1 8/2024
EP 3998975 B1 8/2024
EP 4205685 B1 8/2024
EP 4378515 A3 8/2024

(56) References Cited

FOREIGN PATENT DOCUMENTS

| | | | |
|---|---|---|---|
| EP | 4412547 | A1 | 8/2024 |
| EP | 4412549 | A1 | 8/2024 |
| EP | 4417112 | A2 | 8/2024 |
| EP | 3629964 | B1 | 9/2024 |
| EP | 4427666 | A2 | 9/2024 |
| EP | 4433133 | A1 | 9/2024 |
| EP | 4433141 | A1 | 9/2024 |
| EP | 3184035 | B1 | 10/2024 |
| EP | 4091569 | | 10/2024 |
| EP | 4218579 | B1 | 10/2024 |
| EP | 4444195 | A1 | 10/2024 |
| EP | 4452069 | A1 | 10/2024 |
| EP | 3915477 | B1 | 11/2024 |
| EP | 4193947 | B1 | 11/2024 |
| EP | 4417112 | A3 | 11/2024 |
| EP | 4427666 | A3 | 11/2024 |
| EP | 3860447 | B1 | 12/2024 |
| EP | 4101372 | B1 | 12/2024 |
| EP | 4215138 | B1 | 12/2024 |
| EP | 4437989 | A3 | 12/2024 |
| EP | 4477171 | A2 | 12/2024 |
| EP | 3737453 | B1 | 1/2025 |
| EP | 3760152 | B1 | 1/2025 |
| EP | 3957968 | B1 | 1/2025 |
| EP | 4031044 | | 1/2025 |
| EP | 4458292 | A3 | 1/2025 |
| EP | 4482412 | A1 | 1/2025 |
| EP | 4482413 | A1 | 1/2025 |
| EP | 4482564 | A2 | 1/2025 |
| EP | 4489634 | A1 | 1/2025 |
| EP | 4496546 | A1 | 1/2025 |
| EP | 2915555 | B1 | 2/2025 |
| EP | 4031007 | B1 | 2/2025 |
| EP | 4153526 | B1 | 2/2025 |
| EP | 4480435 | A3 | 2/2025 |
| EP | 4498955 | A1 | 2/2025 |
| EP | 4504085 | A1 | 2/2025 |
| EP | 4483828 | A3 | 3/2025 |
| EP | 4387547 | B1 | 5/2025 |
| EP | 4370187 | B1 | 6/2025 |
| EP | 4555953 | A3 | 6/2025 |
| IL | 246415 | B | 12/2019 |
| IN | 201614021431 | A | 12/2016 |
| IN | 201614021432 | A | 12/2016 |
| IN | 201614021450 | A | 12/2016 |
| JP | 4545384 | B2 | 7/2010 |
| JP | 4887810 | B2 | 2/2012 |
| JP | 4940332 | B2 | 3/2012 |
| JP | 2012055602 | A | 3/2012 |
| JP | 2012200509 | A | 10/2012 |
| JP | 5154031 | B2 | 2/2013 |
| JP | 5193190 | B2 | 5/2013 |
| JP | 5372314 | B2 | 12/2013 |
| JP | 2014014713 | A | 1/2014 |
| JP | 5550150 | B2 | 5/2014 |
| JP | 5762697 | B2 | 6/2015 |
| JP | 5856712 | B2 | 2/2016 |
| JP | 5908270 | B2 | 4/2016 |
| JP | 5944331 | B2 | 7/2016 |
| JP | 6050522 | B2 | 12/2016 |
| JP | 6059737 | B2 | 12/2016 |
| JP | 2017012750 | A | 1/2017 |
| JP | 2017012755 | A | 1/2017 |
| JP | 2017038919 | A | 2/2017 |
| JP | 2017051211 | A | 3/2017 |
| JP | 2017104552 | A | 6/2017 |
| JP | 6246742 | B2 | 12/2017 |
| JP | 6342524 | B2 | 6/2018 |
| JP | 6434495 | B2 | 12/2018 |
| JP | 6445509 | B2 | 12/2018 |
| JP | 6445742 | B1 | 12/2018 |
| JP | 6466114 | B2 | 2/2019 |
| JP | 6479005 | B2 | 2/2019 |
| JP | 6515084 | B2 | 5/2019 |
| JP | 6528010 | B1 | 6/2019 |
| JP | 6655655 | B2 | 2/2020 |
| JP | 2020108766 | A | 7/2020 |
| JP | 6746734 | B2 | 8/2020 |
| JP | 6776021 | B2 | 10/2020 |
| JP | 6776025 | B2 | 10/2020 |
| JP | 6786275 | B2 | 11/2020 |
| JP | 6821812 | B2 | 1/2021 |
| JP | 2021007772 | A | 1/2021 |
| JP | 2021501011 | A | 1/2021 |
| JP | 6843502 | B2 | 3/2021 |
| JP | 2021069921 | A | 5/2021 |
| JP | 6894004 | B2 | 6/2021 |
| JP | 6920312 | B2 | 8/2021 |
| JP | 6926306 | B2 | 8/2021 |
| JP | 6932484 | B2 | 8/2021 |
| JP | 6936872 | B2 | 9/2021 |
| JP | 2021523755 | A | 9/2021 |
| JP | 6980386 | B2 | 12/2021 |
| JP | 2022020838 | A | 2/2022 |
| JP | 2022063862 | A | 4/2022 |
| JP | 7101228 | B2 | 7/2022 |
| JP | 7102558 | B2 | 7/2022 |
| JP | 7106301 | B2 | 7/2022 |
| JP | 7135202 | B2 | 9/2022 |
| JP | 2022540496 | A | 9/2022 |
| JP | 2022159146 | A | 10/2022 |
| JP | 2022176157 | A | 11/2022 |
| JP | 2022546719 | A | 11/2022 |
| JP | 2022548944 | A | 11/2022 |
| JP | 2022177819 | A | 12/2022 |
| JP | 2022179432 | A | 12/2022 |
| JP | 2022187485 | A | 12/2022 |
| JP | 2022187486 | A | 12/2022 |
| JP | 2022188763 | A | 12/2022 |
| JP | 2023002720 | A | 1/2023 |
| JP | 2023010544 | A | 1/2023 |
| JP | 2023501756 | A | 1/2023 |
| JP | 7220242 | B2 | 2/2023 |
| JP | 7230168 | B2 | 2/2023 |
| JP | 2023024395 | A | 2/2023 |
| JP | 2023026388 | A | 2/2023 |
| JP | 2023506505 | A | 2/2023 |
| JP | 2023507412 | A | 2/2023 |
| JP | 7242665 | B2 | 3/2023 |
| JP | 7242816 | B2 | 3/2023 |
| JP | 7246319 | B2 | 3/2023 |
| JP | 2023027023 | A | 3/2023 |
| JP | 2023027202 | A | 3/2023 |
| JP | 2023033335 | A | 3/2023 |
| JP | 7256621 | B2 | 4/2023 |
| JP | 7262919 | B2 | 4/2023 |
| JP | 2023515798 | A | 4/2023 |
| JP | 2023517284 | A | 4/2023 |
| JP | 7275333 | B2 | 5/2023 |
| JP | 7282759 | B2 | 5/2023 |
| JP | 2023074000 | A | 5/2023 |
| JP | 2023519039 | A | 5/2023 |
| JP | 7292822 | B2 | 6/2023 |
| JP | 2023526907 | A | 6/2023 |
| JP | 2023139173 | A | 10/2023 |
| JP | 7391562 | B2 | 11/2023 |
| JP | 7394766 | B2 | 11/2023 |
| JP | 7400050 | B2 | 12/2023 |
| JP | 7423550 | B2 | 1/2024 |
| JP | 2024012693 | A | 1/2024 |
| JP | 7465944 | B2 | 4/2024 |
| JP | 2024059810 | A | 5/2024 |
| JP | 2024060605 | A | 5/2024 |
| JP | 7493935 | B2 | 6/2024 |
| JP | 7499702 | B2 | 6/2024 |
| JP | 7512156 | B2 | 7/2024 |
| JP | 7514764 | B2 | 7/2024 |
| JP | 7515637 | B2 | 7/2024 |
| JP | 7516185 | B2 | 7/2024 |
| JP | 7523073 | B2 | 7/2024 |
| JP | 7523074 | B2 | 7/2024 |
| JP | 2024528078 | A | 7/2024 |
| JP | 7517994 | B2 | 8/2024 |
| JP | 7520967 | B2 | 8/2024 |

(56) References Cited

FOREIGN PATENT DOCUMENTS

| | | | |
|---|---|---|---|
| JP | 7530317 | B2 | 8/2024 |
| JP | 7532506 | B2 | 8/2024 |
| JP | 7535097 | B2 | 8/2024 |
| JP | 2024103761 | A | 8/2024 |
| JP | 7539974 | B2 | 9/2024 |
| JP | 7551326 | B2 | 9/2024 |
| JP | 2024121015 | A | 9/2024 |
| JP | 2024125304 | A | 9/2024 |
| JP | 7566503 | B2 | 10/2024 |
| JP | 2024536350 | A | 10/2024 |
| JP | 2024536352 | A | 10/2024 |
| JP | 2024537099 | A | 10/2024 |
| JP | 7574276 | B2 | 11/2024 |
| JP | 7577739 | B2 | 11/2024 |
| JP | 7587597 | B2 | 11/2024 |
| JP | 2024156696 | A | 11/2024 |
| JP | 2024543437 | A | 11/2024 |
| JP | 7592480 | B2 | 12/2024 |
| JP | 2024544543 | A | 12/2024 |
| JP | 7617073 | B2 | 1/2025 |
| JP | 7617103 | B2 | 1/2025 |
| JP | 2025013792 | A | 1/2025 |
| JP | 7628563 | B2 | 2/2025 |
| JP | 7633185 | B2 | 2/2025 |
| JP | 7637671 | B2 | 2/2025 |
| JP | 7639079 | B2 | 2/2025 |
| JP | 2025023950 | A | 2/2025 |
| JP | 2025026734 | A | 2/2025 |
| JP | 2025026852 | A | 2/2025 |
| JP | 2025027101 | A | 2/2025 |
| JP | 7635238 | B2 | 3/2025 |
| JP | 7640580 | B2 | 3/2025 |
| JP | 7641330 | B2 | 3/2025 |
| JP | 2025028941 | A | 3/2025 |
| JP | 2025036543 | A | 3/2025 |
| JP | 2025036738 | A | 3/2025 |
| JP | 2025507449 | A | 3/2025 |
| JP | 7646980 | B2 | 4/2025 |
| JP | 7647478 | B2 | 4/2025 |
| JP | 7654796 | B2 | 4/2025 |
| JP | 7662472 | B2 | 4/2025 |
| JP | 7662473 | B2 | 4/2025 |
| JP | 2025509157 | A | 4/2025 |
| JP | 2025511803 | A | 4/2025 |
| JP | 7686646 | B2 | 6/2025 |
| RU | 2016124794 | A | 12/2017 |
| RU | 2016124801 | A | 12/2017 |
| RU | 2016125763 | A | 1/2018 |
| WO | 9843530 | A1 | 10/1998 |
| WO | 0168178 | A1 | 9/2001 |
| WO | 2008091197 | A1 | 7/2008 |
| WO | 2014113612 | A1 | 7/2014 |
| WO | 2015057521 | A1 | 4/2015 |
| WO | 2015095577 | A1 | 6/2015 |
| WO | 2015130824 | A1 | 9/2015 |
| WO | 2016001015 | A1 | 1/2016 |
| WO | 2017098198 | A1 | 6/2017 |
| WO | 2018053148 | A1 | 3/2018 |
| WO | 2018053164 | A1 | 3/2018 |
| WO | 2018136741 | A1 | 7/2018 |
| WO | 2019195439 | A1 | 10/2019 |
| WO | 2019226640 | A1 | 11/2019 |
| WO | 2021053482 | A1 | 3/2021 |
| WO | 2021053648 | A1 | 3/2021 |
| WO | 2021061198 | A1 | 4/2021 |
| WO | 2021242852 | A1 | 12/2021 |
| WO | 2022038546 | A1 | 2/2022 |
| WO | 20221 48153 | A1 | 7/2022 |
| WO | 2022180046 | A1 | 9/2022 |
| WO | 2022214870 | A1 | 10/2022 |
| WO | 2022246011 | A1 | 11/2022 |
| WO | 2022251429 | A1 | 12/2022 |
| WO | 2023275848 | A1 | 1/2023 |
| WO | 2023278577 | A1 | 1/2023 |
| WO | 2023280822 | A1 | 1/2023 |
| WO | 2023287289 | A1 | 1/2023 |
| WO | 2023007324 | A1 | 2/2023 |
| WO | 2023009569 | A1 | 2/2023 |
| WO | 2023018741 | A1 | 2/2023 |
| WO | 2023028531 | A1 | 3/2023 |
| WO | 2023059507 | A1 | 4/2023 |
| WO | 2023059509 | A1 | 4/2023 |
| WO | 2023086778 | A1 | 5/2023 |
| WO | 2023086865 | A1 | 5/2023 |
| WO | 2023105322 | A1 | 6/2023 |
| WO | 2023122183 | A1 | 6/2023 |
| WO | 2023164001 | A1 | 8/2023 |
| WO | 2023192858 | A1 | 10/2023 |
| WO | 2023196810 | A1 | 10/2023 |

* cited by examiner 10
16
40
34
36
30
14
12
18
18
38
SECTION A-A

MAGNETIC POSITION SENSOR AND CABLE

CROSS REFERENCE TO RELATED APPLICATION DATA

The present application claims the benefit under 35 USC § 119 (e) of U.S. Provisional Application Nos. 63/330,658 filed Apr. 13, 2022 and 63/399,992 filed Aug. 22, 2022; the full disclosures which are incorporated herein by reference in their entirety for all purposes.

BACKGROUND

A medical positioning system is often used to track the position and/or orientation of a medical device within a patient. Example medical devices used with medical positioning systems include catheters, introducers, guide wires and the like. Such a medical device may include an elongate flexible shaft and various diagnostic and/or therapeutic elements, such as electrodes, that are used to perform various diagnosis or treatment procedures, such as mapping and ablation, on anatomy, such as the heart.

Some medical positioning systems use magnetic fields to induce voltage in a coil of a magnetic position sensor to generate an output signal that is processed by an electronic control unit to determine the position and/or orientation of the magnetic position sensor within a patient. The reliability and accuracy of the magnetic positioning system is dependent upon the signal to noise ratio of the magnetic position sensor. As such, it is beneficial to increase the voltage induced in the coil.

The signal to noise ratio of a magnetic position sensor may be limited by the geometry of the magnetic position sensor, especially in the case where the magnetic position sensor has a relatively small outer diameter (e.g., on the order of 1 French (0.33 millimeters) or less). Accordingly, small diameter magnetic positions sensors with improved signal-to-noise ratio are of interest.

Many medical devices use small diameter signal wires to conduct a position signal from a magnetic position sensor to a medical positioning system. Small diameter wires, however, can be susceptible to deflection-induced and/or tension-induced breakage arising from operation deflections of the medical device.

BRIEF SUMMARY

The following presents a simplified summary of some embodiments of the invention to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments described herein are directed to magnetic position sensors that include features that enhance performance and durability. In many embodiments, a magnetic position sensor is configured with an extended length magnetically permeable core to enhance signal to noise ratio. In many embodiments, a magnetic position sensor includes a reinforced connection cable assembly with improved resistance to deflection-induced and/or tension-induced breakage. In many embodiments, a magnetic position sensor includes the reinforced connection cable assembly and the extended length magnetically permeable core.

Embodiments described herein directed to magnetic position sensors that include an extended length magnetically permeable core include a coil wrapped around the magnetically permeable core. In many embodiments, the axial length of the coil is less than 83 percent of the axial length of the extended length magnetically permeable core. The reduced axial length of the coil may be especially beneficial in a magnetic position sensor with a relatively small outer diameter (e.g., on the order of 1 French (0.33 millimeters) or less) in which small diameter wire (e.g., 58 AWG) is used to form the coil in order to keep the electrical resistance of the coil below a suitable limit. The extension of the magnetically permeable core beyond the reduced length coil serves to concentrate magnetic field through the coil, which increases the resulting voltage induced in the coil.

Thus, in one aspect, a magnetic position sensor includes a magnetically permeable core and a coil. The magnetically permeable core has a central axis and a core length along the central axis. The coil includes a wire wrapped around the magnetically permeable core and configured to output an electric signal in response to a magnetic field. The coil has a coil length along the central axis that is less than 90 percent of the core length so that the magnetically permeable core extends beyond the coil. In some embodiments, the coil length along the central axis that is less than 80 percent of the core length. In many embodiments, the coil has an outer diameter of less than 0.013 inch.

In many embodiments, the magnetic position sensor has a suitable configuration for use in a medical positioning system. For example, the size of the magnetic position sensor can be small relative to magnetic position sensors that are not configured for use in a medical positioning system. Despite the small size, the coil may have greater than 1000 turns, may have greater than 1400 turns, may have a coil resistance less than 230 ohms at 20 degrees Celsius, and/or may include any suitable number of wire layers (e.g., 4, 5, 6, 7, 8 or more wire layers). In some embodiments, the magnetically permeable core has a solid cross section.

In another aspect, a magnetic position sensor includes a magnetically permeable core and a coil. The magnetically permeable core has a central axis and a core length along the central axis. The coil includes a wire wrapped around the magnetically permeable core and configured to output an electric signal in response to a magnetic field. The coil has a coil length along the central axis that is less than 90 percent of the core length. In some embodiments, the coil length is less than 80 percent of the core length.

In many embodiments, the magnetic position sensor has a suitable configuration for use in a medical positioning system. For example, the magnetically permeable core can consist essentially of a suitable magnetically permeable material (e.g., a nickel-iron soft ferromagnetic alloy, mu-metal). The coil can have an outer diameter of less than 0.015 inch. The coil can have an outer diameter of less than 0.012 inch. The coil can have greater than 1000 turns and can have greater than 1400 turns. The coil can have a coil resistance less than 250 ohms at 20 degrees Celsius. The coil can include any suitable number of wire layers (e.g., 4, 5, 6, 7, 8 or more wire layers). The magnetically permeable core can have a solid cross section. The core length can be less than 0.200 inch. In some embodiments, the core length is less than 0.160 inch. The magnetically permeable core can extend a suitable percent (e.g., 10%, 12%, 14%, 20% or more) of the core length from an end of the coil. While the magnetically permeable core can extend equally from both ends of the coil, in many embodiments the magnetically permeable core extends primarily from one end of the core. The magnetic position sensor can further include an encapsulation that encloses the magnetically permeable core and the coil. The encapsulation can have an outer diameter of less than 0.015 inch. The encapsulation can include a surrounding outer membrane. The encapsulation can include an adhesive (e.g., epoxy) within the surrounding outer membrane.

In another aspect, a catheter includes an elongated catheter shaft, a medical assembly, and a magnetic position sensor. The elongated catheter shaft is configured to be received within a patient. The medical assembly is coupled with the elongated catheter shaft and configured for use within the patient to diagnose and/or treat a medical condition of the patient. The magnetic position sensor includes a magnetically permeable core and a coil. The magnetically permeable core has a central axis and a core length along the central axis. The coil includes a wire wrapped around the magnetically permeable core and configured to output an electric signal in response to a magnetic field. The coil has a coil length along the central axis that is less than 90 percent of the core length. In some embodiments, the coil length is less than 80 percent of the core length.

The magnetic position sensor can have any suitable configuration for use in the catheter. For example, the magnetically permeable core can consist essentially of a suitable magnetically permeable material (e.g., a nickel-iron soft ferromagnetic alloy, mu-metal). The coil can have an outer diameter of less than 0.015 inch. In some embodiments, the coil has an outer diameter of less than 0.012 inch. The coil can have greater than 1000 turns and can have greater than 1400 turns. The coil can have a coil resistance less than 250 ohms at 20 degrees Celsius. The coil can include any suitable number of wire layers (e.g., 4, 5, 6, 7, 8 or more wire layers). The magnetically permeable core can have a solid cross section. The core length can be less than 0.200 inch. In some embodiments, the core length is less than 0.160 inch. The magnetically permeable core can extend a suitable percent (e.g., 10%, 12%, 14%, 20% or more) of the core length from an end of the coil. In some embodiments, the magnetically permeable core extends equally from both ends of the coil. The magnetic position sensor can include an encapsulation that encloses the magnetically permeable core and the coil. The encapsulation can have an outer diameter of less than 0.015 inch. The encapsulation can include a surrounding outer membrane. The encapsulation can include an adhesive (e.g., epoxy) within the surrounding outer membrane.

Embodiments described herein directed to magnetic position sensors that include a reinforced connection cable include a magnetically permeable core and a coil. The connection cable includes a pair of signal wires and a third wire. The coil is configured to output an electric signal in response to a magnetic field. The pair of signal wires is connected to and extends from the coil. The third wire extends along a length of the pair of signal wires and is configured to reinforce the pair of signal wires. The third wire is configured to inhibit deflection-induced and/or tension-induced failure of the pair of signal wires by reducing deflection induced strains in the pair of signal wires via the restrain provided by the third wire and increasing total tension strength of the wire bundle.

Thus, in another aspect, a magnetic position sensor includes a magnetically permeable core, a coil, a pair of signal wires, and a third wire. The coil includes a wire wrapped around the magnetically permeable core. The coil is configured to output an electric signal in response to a magnetic field. The pair of signal wires is connected to and extends from the coil. The pair of signal wires is configured to transmit the electric signal. The third wire extends along a length of the pair of signal wires. The third wire is configured to reinforce the pair of signal wires to inhibit deflection-induced and/or tension-induced breakage of the pair of signal wires.

In many embodiments, the third wire and the pair of signal wires form an elongated three-wire cable segment in which the third wire and the pair of signal wires are intertwisted. For example, in many embodiments, the third wire and the pair of signal wires are intertwisted in a range of 10 to 30 turns per inch length of the elongated three-wire cable segment. In some embodiments, the third wire and the pair of signal wires are intertwisted in a range of 18 to 20 turns per inch length of the elongated three-wire cable segment.

The third wire can have any suitable configuration for reinforcing the pair of signal wires. For example, in some embodiments, the diameter of the third wire is equal to or greater than the diameter of the signal wires. For example, in some embodiments, the signal wire diameter is 42 American wire gauge (AWG) and the third wire diameter is 42 AWG, 40 AWG, or 38 AWG. The diameter of the third wire can be less than the diameter of the signal wires and still serve to reinforce the signal wires against deflection-induced and/or tension-induced breakage. Each of the pair of signal wires can be made from a signal wire material. The third wire can be made from a third wire material that is stronger than the signal wire material. For example, in some embodiments, each of the pair of signal wires includes a copper wire and the third wire includes a nickel wire. In some embodiments, each of the pair of signal wires includes a copper wire and the third wire includes a stainless steel wire. In some embodiments, the third wire includes a braided cable or a woven cable.

The third wire can extend along any suitable segment of the pair of signal wires. For example, in some embodiments, the magnetic position sensor further includes an exterior tube having an exterior tube lumen in which the magnetically permeable core and the coil are disposed. Each of the pair of signal wires can extend into the exterior tube lumen and overlap a length of the magnetically permeable core disposed within the exterior tube lumen. The third wire can extend into the exterior tube lumen so as to not overlap the magnetically permeable core. A distal end of the third wire can be adhesively secured within the exterior tube lumen. In some embodiments, the exterior tube includes a polyimide tube. In some embodiments, the third wire does not extend into the exterior tube lumen and ends proximal to the exterior tube.

The third wire can have color selected to help facilitate manufacture of the magnetic position sensor. For example, the pair of signal wires and the third wire can have a color combination indicative of an identification of the magnetic position sensor.

The third wire can have an insulation layer selected to enhance protection of the pair of signal wires. For example, each of the pair of signal wires can include a respective signal wire insulation layer. The third wire can include a third wire insulation layer that resists kinking more than each of the respective signal wire insulation layers. For example, each of the respective signal wire insulation layers can include a polyurethane insulation layer. The third wire insulation layer can include a polyimide insulation layer.

The magnetic position sensor can be employed in any suitable medical device. For example, in many embodiments, a catheter includes an elongated catheter shaft assembly, a medical assembly coupled with the elongated catheter shaft assembly, and any suitable embodiment of the magnetic position sensor described above. In many embodiments, the medical assembly is configured for use within the patient to diagnose and/or treat a medical condition of the patient.

In some embodiments, the medical assembly includes a flexible spline assembly that extends from the elongated catheter shaft assembly. The flexible spline assembly can have a flexibility that accommodates inducing deflection of the flexible spline assembly to conform the flexible spline assembly to a tissue surface. The flexible spline assembly can include the magnetic position sensor. The third wire can extend through the flexible spline assembly and into the elongated catheter shaft assembly.

In some embodiments, the elongated catheter shaft assembly includes a steerable section that is selectively bendable. The third wire can extend through the steerable section.

In many embodiments, the catheter includes a handle assembly that is coupled with a proximal end of the elongated catheter shaft assembly. The third wire can extend into the handle assembly.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Magnetic Position Sensors with Extended Magnetically Permeable Core

Figure 1:
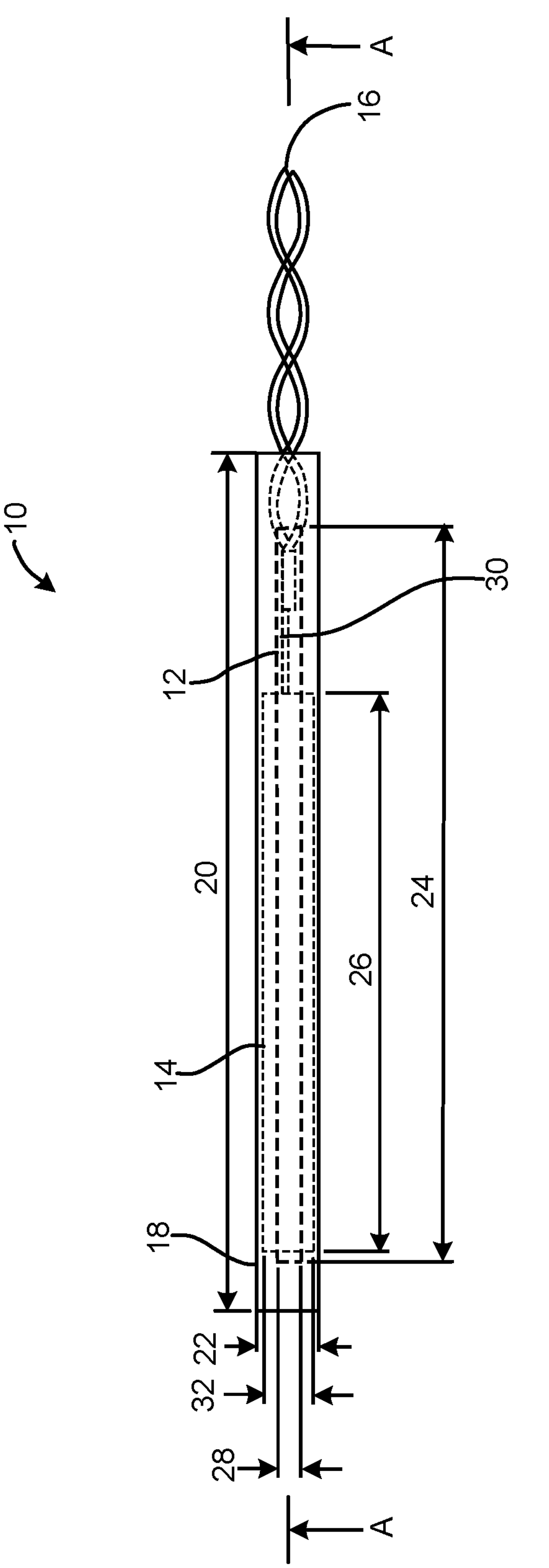
FIG. 1 illustrates a magnetic position sensor with an extended length magnetically permeable core, in accordance with embodiments.
Figure 2:
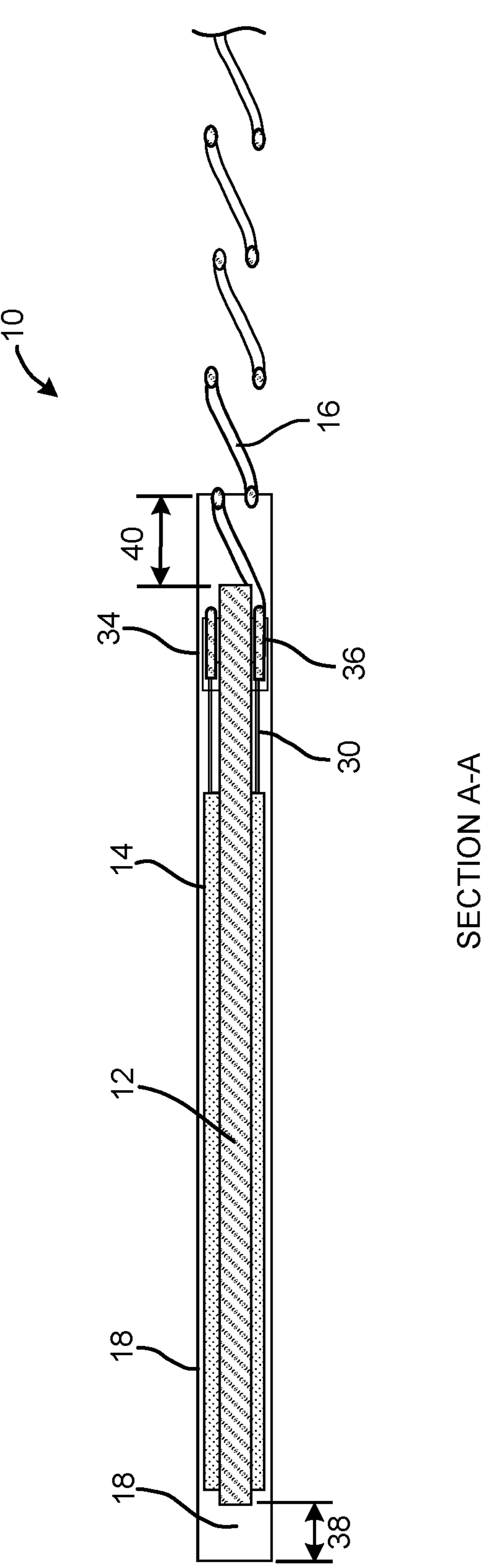
FIG. 2 is a longitudinal cross-sectional view of the magnetic position sensor of FIG. 1.
Figure 2:

Referring now to the drawings wherein like reference numerals are used to identify similar components in the various views, FIG. 1 shows a magnetic position sensor 10, in accordance with embodiments. FIG. 2 shows a longitudinal cross-sectional view of the magnetic position sensor 10. The magnetic position sensor 10 includes a magnetically permeable core 12, a coil 14, a twisted pair of connection wires 16 (also referred to herein as signal wires 16), and an encapsulation 18. The magnetic position sensor 10 has an axial length 20 and an outer diameter 22. In some embodiments, the outer diameter 22 is on the order of 1 French (0.33 millimeters or less) to enable usage of the magnetic position sensor 10 in small diameter catheter components.

The magnetically permeable core 12 has an axial length 24 that exceeds an axial length 26 of the coil 14 by a suitable length to increase the amount of magnetic flux (from a magnetic field(s) generated by a medical positioning system) conducted through the coil 14 by the core 12. For example, in many embodiments, the axial length 26 of the coil is less than 90 percent of the axial length 24 of the core 12. In some embodiments, the axial length 26 of the coil 14 is less than 86 percent of the axial length 24 of the core 12. In some embodiments, the axial length 26 of the coil 14 is less than 83 percent of the axial length 24 of the core 12. In some embodiments, the axial length 26 of the coil 14 is less than 80 percent of the axial length 24 of the core 12. In some embodiments, the axial length 26 of the coil is 77 percent of the axial length 24 of the core 12.

In many embodiments, the magnetically permeable core 12 has a circular cross-sectional shape and is formed from a suitable high-permeability magnetic material (e.g., a nickel-iron soft ferromagnetic alloy, mu-metal) that has a suitable high magnetic relative permeability values (e.g., 50,000; 80,000 to 100,000). The core 12 has an outer diameter 28 that provides a suitable cross-sectional area of the core 12 to conduct a suitable amount of magnetic flux through the coil 14 while leaving a suitable annular space for the coil 14 and the encapsulation 18 within the outer diameter 22 of the magnetic position sensor 10.

The coil 14 is formed by wrapping a small diameter coil wire 30 (e.g., 58 AWG) around the core 12 a suitable number of 360 degree turns (e.g., greater than 1000 turns, greater than 1200 turns, greater than 1400 turns, greater than 1450 turns) so that a suitable voltage is induced within the coil 14 by a magnetic field generated by a medical positioning system, the coil 14 has a suitable number of layers of the coil wire 30 to have a suitable outer diameter 32, and the coil 14 has an electrical resistance that does not exceed a suitable limit for use with a medical positioning system. For example, in some embodiments, the coil 14 has a total electrical resistance of 209 ohms plus or minus 20 ohms and the coil 14 has six layers of the coil wire 30 so that the outer diameter 32 of the coil 14 is about 0.0105 inch plus or minus 0.001 inch. The coil 14 can, however, have other suitable number of layers of the coil wire 30 such, as, for example, 2, 4, 8, or more layers.

Each end of the coil wire 30 is connected to a respective one of the connection wires 16 via a suitable connection 34 (e.g., solder). For example, in some embodiments, each end of the coil wire 30 is wrapped around a respective one of the connection wires 16 a suitable number of times (e.g., 3 to 5 turns) and soldered to the connection wire 16. In some embodiments, an insulation 36 is provided between and/or around the connection 34 and the core 12. The insulation can be provided using any suitable approach. For example, a suitable insulating coating (e.g., an alumina coating, a parylene coating, a UV adhesive, a heat shrink cover, a polymer tubing) can be employed and/or a heat shrink wrap can enclose each connection 34.

The encapsulation 18 encloses an assembly including the core 12, the coil 14 wrapped around the core 12, the connections 34, and a distal portion of the pair of connection wires 16. The encapsulation 18 can be formed from any suitable material, such as, for example, a suitable adhesive (e.g., epoxy). The encapsulation 18 extends distal to the distal end of the core 12 by a suitable distal end distance 38 (e.g., by 0.010 inch minimum). The encapsulation also extends proximal to the proximal end of the core 12 by a suitable proximal end distance 40 (e.g., 0.015 inch). The encapsulation 18 can also be flushed with the core or flushed with coil with core exposed. In some embodiments, the encapsulation 18 includes a surrounding outer membrane (e.g., a thin polyimide membrane) and can include a suitable adhesive (e.g., epoxy) within the surrounding outer membrane.

The connection wires 16 are configured for electrically connecting the coil 14 with a medical positioning system. The connection wires 16 can have any suitable configuration. For example, in some embodiments, the connection wires 16 are about 120 inches long, have a wire diameter of 41 to 44 AWG, and are twisted at 25 twists per inch. In some embodiments, the total resistance of the coil 14 and the connection wires 16 is 302 ohms plus or minus 20 ohms.

The magnetic position sensor 10 can have any suitable axial length 20 so as to accommodate the extended axial length 24 of the core 12 relative to the axial length 26 of the coil 14 and the lengths of the end portions 38, 40 of the encapsulation 18. The extended axial length 24 of the core 12 relative to the axial length 26 of the coil 24 increases the axial length 20 relative to a configuration in which the core 12 has an axial length closer to the axial length 26 of the coil 14. In the illustrated embodiment, the additional axial length of the core 12 relative to the coil 14 is disposed proximal to the coil 14. The additional axial length of the core 12 relative to the coil 14 can, however, be disposed in any suitable manner relative to ends of the coil 14 such as distal to the coil 14 or split between distal to the coil 14 and proximal to the coil 14 by any suitable portions of the additional axial length of the core 12 relative to the coil 14.

Magnetic Position Sensor Assemblies with Reinforced Connection Cable

Figures 3, 4:
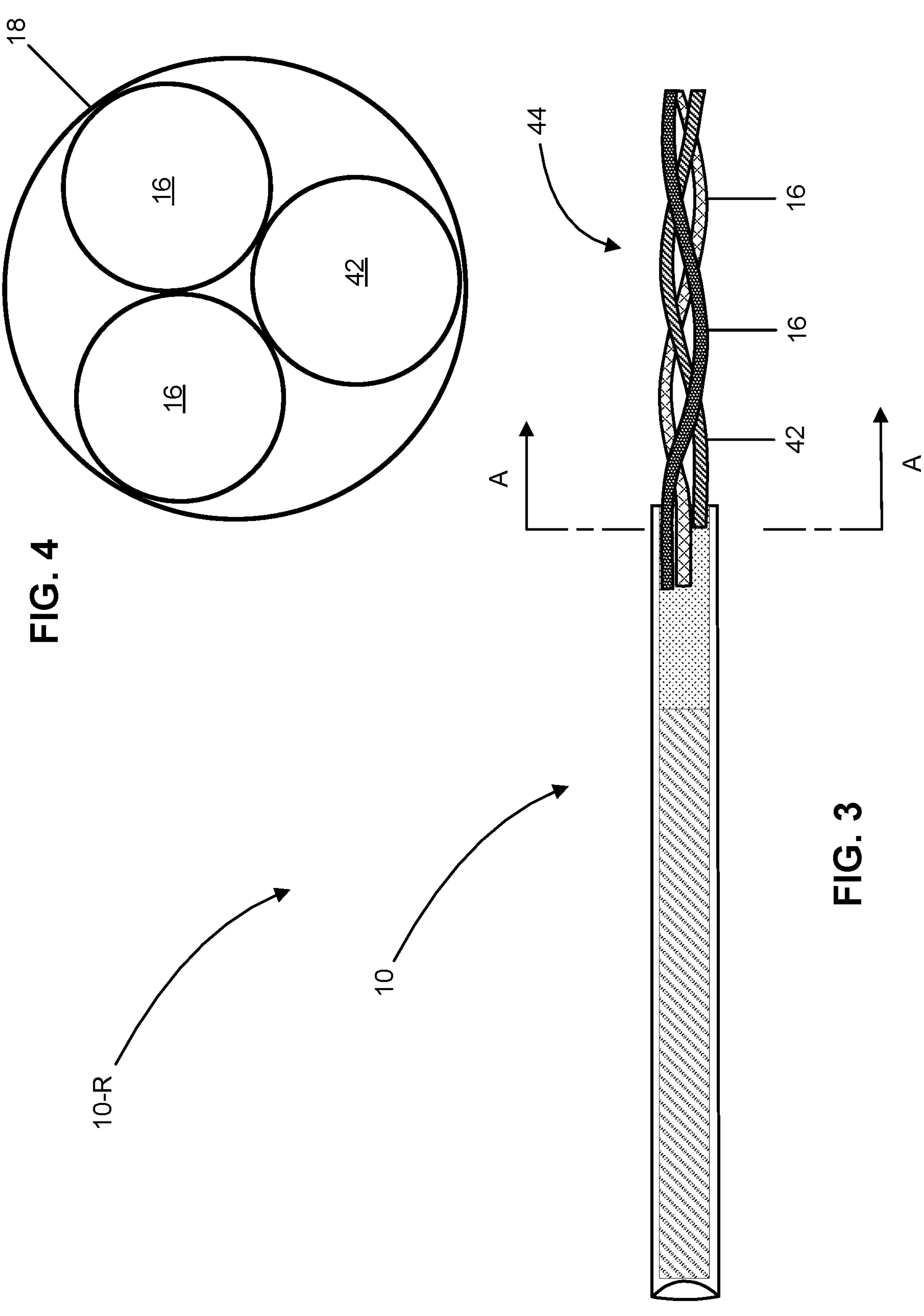
FIG. 3 illustrates an embodiment of the magnetic position sensor of FIG. 1 that includes a reinforced connection cable assembly, in accordance with embodiments.
FIG. 4 is an axial cross-sectional view of the magnetic position sensor of FIG. 3.

FIG. 3 illustrates a magnetic position sensor 10-R, in accordance with embodiments. The magnetic position sensor 10-R is configured the same as the magnetic position sensor 10 but for further including a third wire 42 that extends along and is intertwisted with the twisted pair of wires 16. The third wire 42 serves to reinforce the twisted pair of wires 16 to protect the twisted pair of wires 16 from deflection-induced and/or tension-induced breakage. In many embodiments, the third wire 42 has a distal end that is disposed proximally to the proximal end of the core 12 so as to not increase the outside diameter of the magnetic position sensor 10-R.

In many embodiments, the outer diameter 22 of the magnetic position sensor 10-R (on the order of 33 mm in some embodiments) limits the wire diameter of the twisted pair of wires 16, which transmit the electrical signal generated by the magnetic position sensor 10-R. For example, in some embodiments, each of the twisted pair of wires 16 has a wire size of 42 American wire gauge (AWG). Each of the twisted pair of wires 16 can be made from any suitable conductive material (e.g., copper wire). 42 AWG copper wire, due to its small size, is susceptible to deflection-induced and/or tension-induced breakage. In some medical devices, such as the high-density grid paddle catheter illustrated in FIG. 5 and the catheter with a steerable section illustrated in FIG. 6, at least one instance of the magnetic position sensor 10-R can be disposed within or distal to a high-deflection region (e.g., the high-density grid electrode assembly 100 illustrated in FIG. 5, the steerable section 158 of the catheter 150 illustrated in FIG. 6). The high-density electrode assembly 100 and the steerable section 158 may undergo a substantial amount of variable bending during a procedure. In such instances, the twisted pair of wires 16 may be subjected to substantial induced deflection and/or tension that may cause breakage of the twisted pair of wires 16 over time.

The third wire 42 reinforces the twisted pair of wires 16 so as to increase the resistance of the twisted pair of wires 16 to deflection-induced and/or tension-induced breakage. In many embodiments, the third wire 42 is used solely to reinforce the twisted pair of wires 16 instead of providing any electrical connection. The addition of the third wire 42 to the twisted pair of wires 16 forms a reinforced connection cable 44 with an increased tensile strength, increased bending stiffness, and increased kink resistance relative to just the twisted pair of wires 16. The third wire 42 can be made from any suitable material (e.g., copper, nickel, stainless steel) and can have any suitable configuration (e.g., solid wire, stranded wire, braided, woven). The third wire 42 can be made from a higher strength material (e.g., nickel) than the twisted pair of wires 16 (which can made from copper to provide a suitably low resistance) to further increase the mechanical strength of the reinforced connection cable 44.

In addition to increasing the tensile strength of the reinforced connection cable 44, the addition of the third wire 42 serves to increase resistance to kinking of the connection cable 44. Increased kink resistance can be especially beneficial where the connection cable 44 is subjected to induced curvature, which can occur where the connection cable 44 extends through one of the flexible splines 102 shown in FIG. 5 or through the steerable section 158 of the catheter 150 shown in FIG. 6. As illustrated in the cross-section shown in FIG. 4, the twisted pair of wires 16 combines with the third wire 42 so that the reinforced connection cable 44 has an increased and therefore stiffer and stronger cross-section as compared to just the twisted pair of wires 16 and therefore has substantially increased resistance to bending induced kinking relative to just the twisted pair of wires 16.

The third wire 42 can be made from materials other than the material of the twisted pair of wires 16 and/or have a wire diameter other than the wire diameter of the twisted pair of wires 16 to further increase the resistance of the reinforced connection cable 44 to deflection-induced and/or tension-induced breakage relative to just the twisted pair of wires 16. For example, the third wire 42 can be a nickel wire or other high strength wire so that the strength and/or cross-sectional bending stiffness of the third wire 42 is greater than the strength and/or cross-sectional bending stiffness of each of the twisted pair of wires 16. The third wire 42 can have a larger diameter such as, for example, 40 AWG (which is 50% greater in cross-sectional area than the cross-sectional area of a 42 AWG wire) or 38 AWG (which is 150% greater in cross-sectional area than the cross-sectional area of a 42 AWG wire) to provide an even greater increase to the strength and/or axial bending stiffness of the reinforced connection cable 44.

The third wire 42 can include a different outer layer or coating than the twisted pair of wires 16 of further increase the amount of reinforcement provided by the addition of the third wire 42 to the twisted pair of wires 16. For solderability, the twisted pair of wires 16 can have an insulation material, such as polyurethane, that accommodates stripping of end portions of the insulation material to accommodate soldering of the wires 16 to the coil wires 30. In contrast, the third wire 42 can have an insulation layer or outer layer made from a material that provides increased resistance to kinking, such as polyimide, so as to provide an additional resistance to kinking so that the reinforced connection cable 44 is less likely to kink during assembly.

The third wire 42 can also have a color or color combination and therefore can be used in conjunction with a color(s) or a color combination of the signal wires 16 to implement a color-based identification for the magnetic position sensor 10-R. The addition of the third wire 42 increases the number of possible color combinations that can be employed, which may make it is easier to identify the magnetic position sensor 10-R during assembly thereby helping to ease manufacture of the magnetic position sensor 10-R.

FIG. 3 defines the location of a cross-section AA through the magnetic position sensor 10-R for the cross-sectional view AA shown in FIG. 4. The cross-section AA is through a proximal end portion of the encapsulation 18 (which includes a polyimide tube in the illustrated embodiment) and the twisted reinforced connection cable 44, which includes the two signal wires 16 and the third wire 42. The cross-section AA is disposed proximal to a proximal end of the core 12. In the illustrated embodiment, the third wire 42 extends into the polyimide tube and terminates short of the proximal end of the core 12. The third wire 42 can terminate proximal to the proximal end of the polyimide tube. By terminating the third wire 42 proximal to the proximal end of the core 12, the polyimide tube in the magnetic position sensor 10-R can have the same diameter (e.g., 0.011 inch ID and 0.013 inch OD) as the polyimide tube in the magnetic position sensor 10 due to not having to accommodate any overlap of the third wire 42 with the core 12. Since the third wire 42 and the two signal wires 16 are arranged in a triangular arrangement, the addition of the third wire 42 to the signal wires 16 only increases the total cross-sectional diameter of the connection cable 44 about 10% as compared to just the two signal wires 16.

The connection cable 44 provides significant mechanical advantages relative to just the two signal wires 16. For example, in embodiments in which the third wire 42 is made from the same material and wire diameter as the signal wires 16, the connection cable 44 has 50 percent increase in axial strength relative to just the two signal wires 16. An even greater increase in axial strength is gained where the third wire 42 is larger in size than the signal wires 16. For example, in embodiments in which the third wire 42 is a 40 AWG copper wire and each of the signal wires 16 is a 42 AWG copper wire, the connection cable 44 has a 150 percent increase in axial strength relative to just the two signal wires 16. In embodiments in which the third wire 42 is a 38 AWG copper wire and each of the signal wires 16 is a 42 AWG copper wire, the connection cable 44 has a 250 percent increase in axial strength relative to just the two signal wires 16. The third wire 42 can be made from a stronger material than the signal wires 16. For example, the third wire 42 can be made from nickel, which has twice strength as copper (520 N/mm$^2$ vs. 260 N/mm$^2$)

Example Medical Devices

Figure 5:
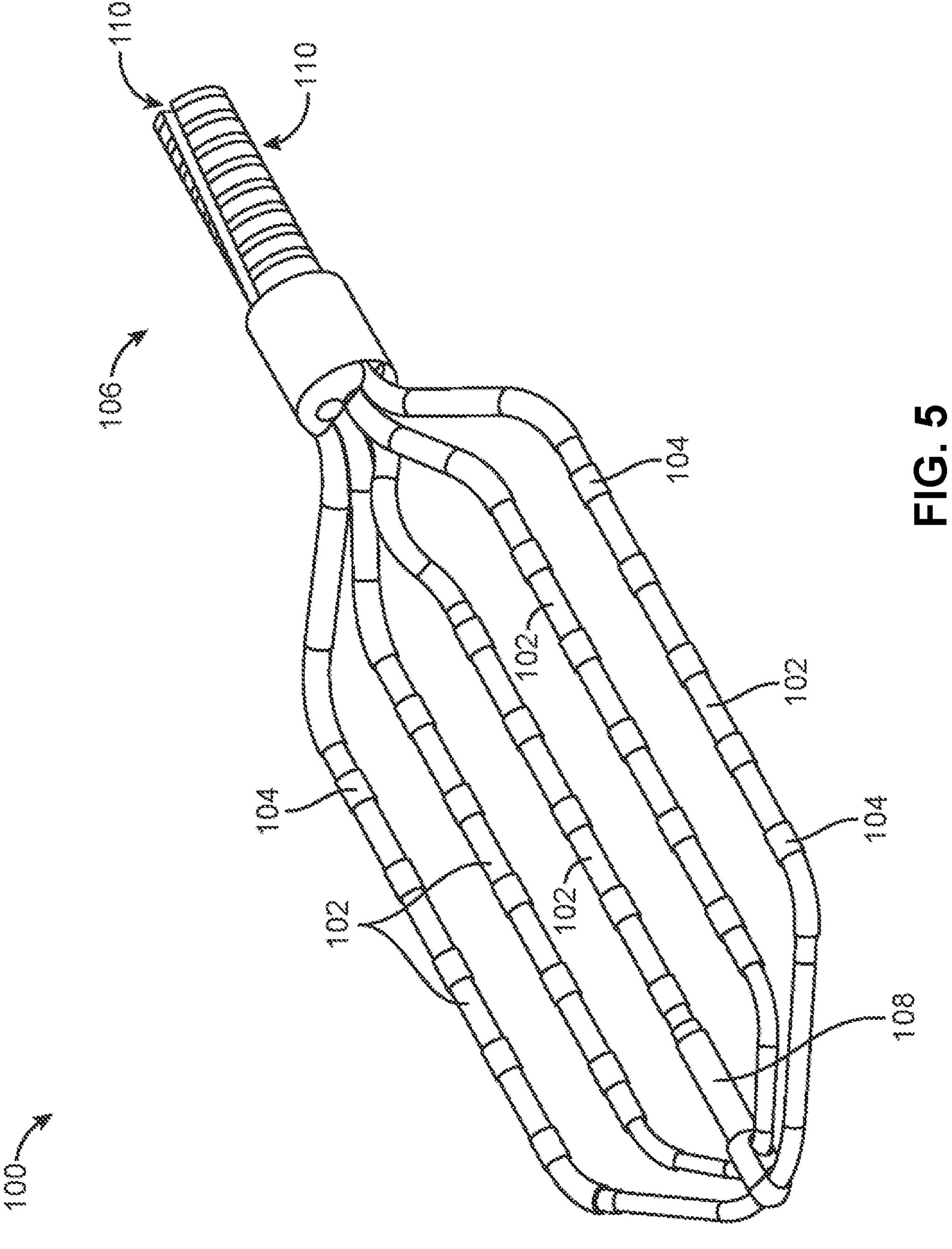
FIG. 5 illustrates a high-density grid electrode assembly of an example medical catheter that can include one or more instances of the magnetic position sensor of FIG. 1 and/or one or more instances of the magnetic position sensor of FIG. 3.

FIG. 5 shows a high-density grid electrode assembly 100 of an example medical catheter that can include one or more instances of the magnetic position sensor 10 and/or the magnetic position sensor 10-R. The electrode assembly 100 includes five flexible splines 102 and spaced apart electrodes 104. Each of the flexible splines 102 supports five of the electrodes 104. The electrode assembly 100 is configured to self-expand from a collapsed deliver configuration wherein the flexible splines 102 are constrained within a lumen of an introducer catheter to the expanded configuration shown in FIG. 5. The flexible splines 102 have a bending compliance that accommodates conforming the splines 102 to a tissue surface, such as an interior surface of a heart to place each of the electrodes 104 in contact with the tissue surface for using the electrodes 104 to perform a diagnostic and/or therapeutic medical procedure on the tissue. The electrode assembly 100 is mounted to the distal end of an elongate catheter shaft assembly 106. As described herein, the magnetic position sensor 10, 10-R can have a small outer diameter that accommodates installation of the magnetic position sensor 10, 10-R within any one or more of the flexible splines 102. For example, an instance of the magnetic position sensor 10, 10-R can be installed within a distal end portion 108 of the central flexible spline 102. An instance of the magnetic position sensor 10, 10-R can be installed within a lumen of any of the flexible splines 102 at a suitable longitudinal location, such as, for example, between adjacent instances of the electrodes 104. One or two instances of the magnetic position sensor 10, 10-R can be installed in slots 110 in the distal end of the elongate catheter shaft assembly 106. The instances of the magnetic position sensor 10, 10-R included in the electrode assembly 100 can be used to generate signals indicative of the position and/or orientation of the corresponding locations of the electrode assembly 100 within a patient using a medical positioning system as described herein.

Figure 6:
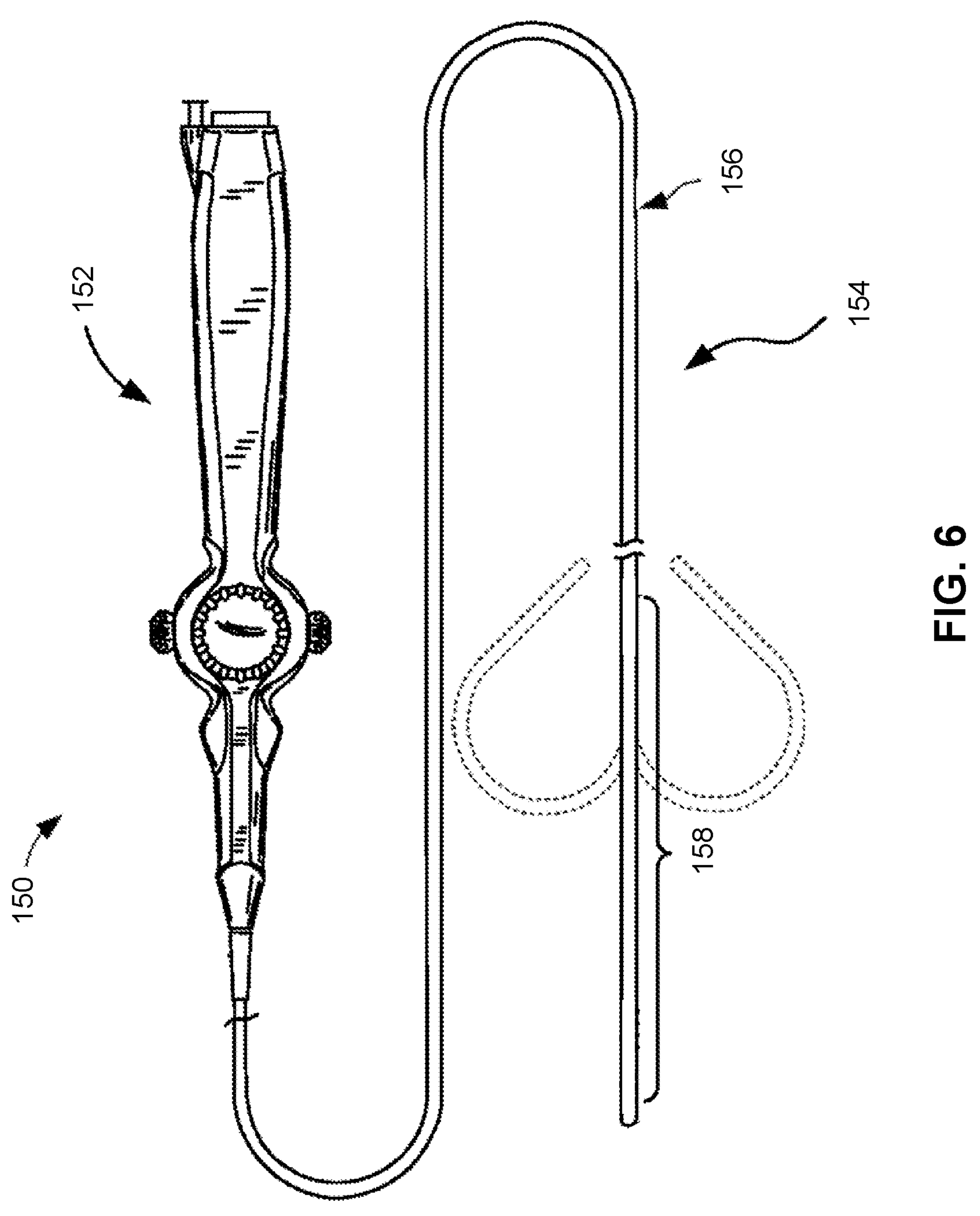
FIG. 6 illustrates another example medical catheter that can include one or more instances of the magnetic position sensor of FIG. 1 and/or one or more instances of the magnetic position sensor of FIG. 3.

FIG. 6 illustrates another example medical catheter 150 that can include one or more instances of the magnetic position sensor 10, 10-R. The catheter 150 includes a handle assembly 152 and an elongated shaft assembly 154. The shaft assembly 154 includes a flexible shaft 156 and a steerable section 158. The handle assembly 152 is drivingly coupled with the steerable section 158 and operable to selectively bend the steerable section 158 in two directions. As described herein, the magnetic position sensor 10, 10-R can have a small outer diameter that accommodates installation of the magnetic position sensor within and/or distal to the steerable section 158. The instances of the magnetic position sensor 10, 10-R included in the catheter 150 can be used to generate signals indicative of the position and/or orientation of corresponding locations of the catheter 150 within a patient using a medical positioning system as described herein.

Localization Systems

The magnetic position sensor(s) 10, 10-R can be used in conjunction with any suitable medical device localization system, such as those referenced and/or described herein. For example, the magnetic position sensor(s) 10, 10-R can be used in conjunction with the catheter localization systems and methods described in U.S. Pat. Pub. No. 2020/0138334 A1 entitled “Method for Medical Device Localization based on Magnetic and Impedance Sensors”, the entire disclosure of which is incorporated herein by reference.

Figure 7:
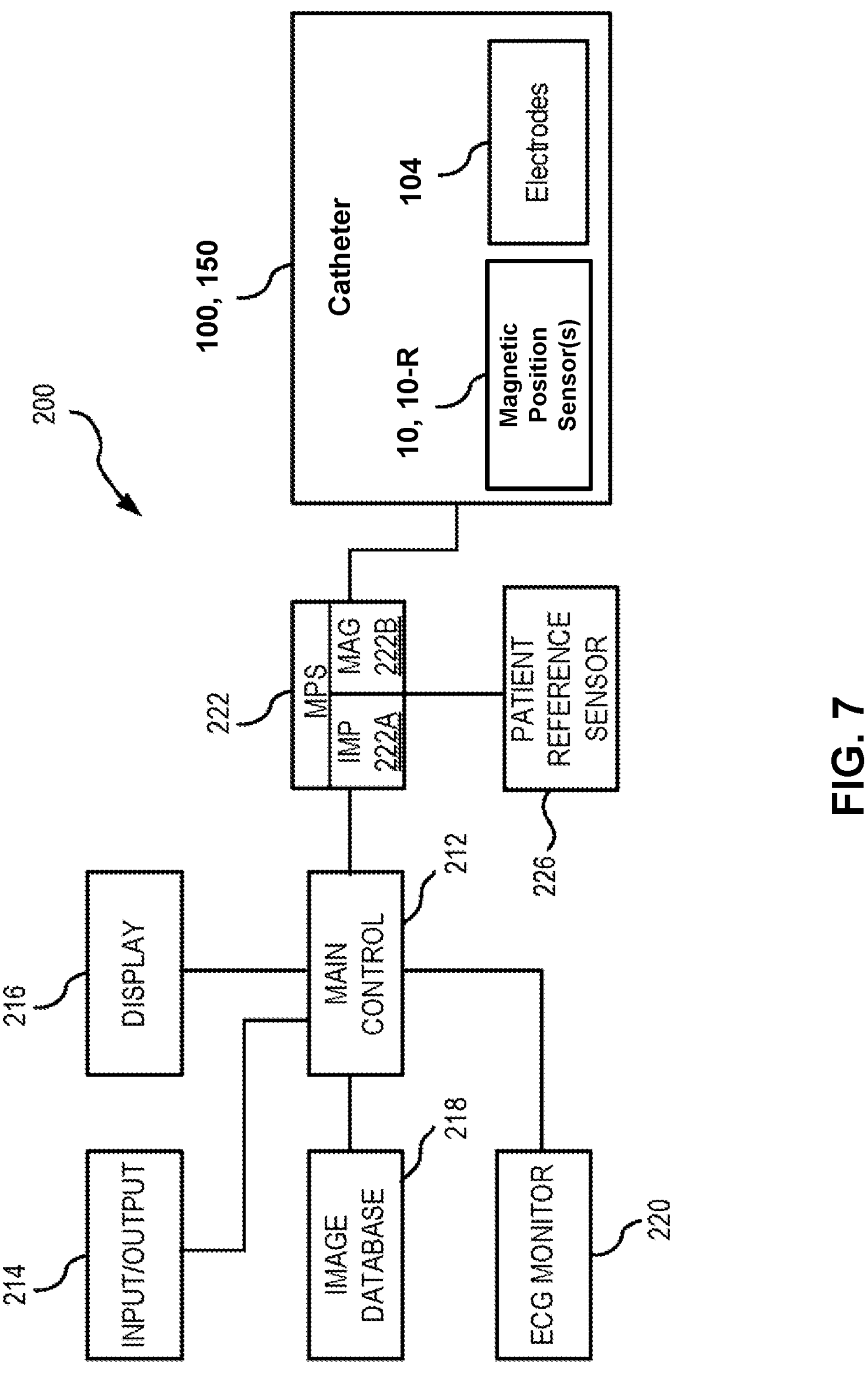
FIG. 7 illustrates an example medical device localization system that can be employed in conjunction with a medical device that includes one or more instances of the magnetic position sensor of FIG. 1 and/or one or more instances of the magnetic position sensor of FIG. 3.

FIG. 7 is a diagrammatic view of a medical device localization system 200 that can be used in conjunction with the magnetic position sensor(s) 10, 10-R. The system 200 includes a main electronic control unit 212 (e.g., a processor) having various input/output mechanisms 214, a display 216, an optional image database 218, an electrocardiogram (ECG) monitor 220, a localization system, such as a medical positioning system 222, and a catheter 100, 150. As described herein, in some embodiments the catheter 100, 150 includes the electrodes 104 and one or more of the magnetic position sensors 104.

The input/output mechanisms 214 may include conventional apparatus for interfacing with a computer-based control unit including, for example, one or more of a keyboard, a mouse, a tablet, a foot pedal, a switch and/or the like. The display 216 may also comprise conventional apparatus, such as a computer monitor.

Various embodiments described herein may find use in navigation applications that use real-time and/or pre-acquired images of a region of interest. Therefore, the system 200 may optionally include the image database 218 to store image information relating to the patient's body. Image information may include, for example, a region of interest surrounding a destination site for the catheter 100, 150 and/or multiple regions of interest along a navigation path contemplated to be traversed by the catheter 100, 150. The data in the image database 218 may include known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database 218 acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from the ECG monitor 220. It should be understood that the foregoing embodiments are examples only and not limiting in nature. For example, the image database 218 may also include three-dimensional image data as well. It should be further understood that the images may be acquired through any imaging modality, now known or hereafter developed, for example X-ray, ultra-sound, computerized tomography, nuclear magnetic resonance or the like.

The ECG monitor 220 is configured to continuously detect an electrical timing signal of the heart organ through the use of a plurality of ECG electrodes (not shown), which may be externally affixed to the outside of a patient's body. The timing signal generally corresponds to a particular phase of the cardiac cycle, among other things. Generally, the ECG signal(s) may be used by the control unit 212 for ECG synchronized play-back of a previously captured sequence of images (cine loop) stored in the database 218. The ECG monitor 220 and ECG-electrodes may both include conventional components.

Another medical positioning system sensor, namely, a patient reference sensor (PRS) 226 (if provided in the system 200) can be configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. The PRS 26 may be attached to the patient's manubrium sternum or other location. The PRS 26 can be configured to detect one or more characteristics of the magnetic field in which it is disposed, wherein medical positioning system 222 determines a location reading (e.g., a P&O reading) indicative of the PRS's position and orientation in the magnetic reference coordinate system.

The medical positioning system 222 is configured to serve as the localization system and therefore to determine position (localization) data with respect to the one or more magnetic position sensors 10, 10-R and/or the electrodes 104 and output a respective location reading. In an embodiment, the medical positioning system 222 may include a first medical positioning system or an electrical impedance-based medical positioning system 222A that determines locations of the electrodes 104 in a first coordinate system, and a second medical positioning system or magnetic field-based medical positioning system 222B that determines location(s) of the magnetic position sensor(s) 10, 10-R in a second coordinate system. In an embodiment, the location readings may each include at least one or both of a position and an orientation (P&O) relative to a reference coordinate system (e.g., magnetic based coordinate system or impedance based coordinate system). In some embodiments, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of the magnetic position sensor(s) 10, 10-R in a magnetic field relative to a magnetic field generator(s) or transmitter(s) and/or the electrodes 104 in an applied electrical field relative to an electrical field generator (e.g., a set of electrode patches). In some embodiments, the P&O may be expressed with six degrees-of-freedom (six DOF) as a 3D position (e.g., X, Y, Z coordinates) and 3D orientation (e.g., roll, pitch, and yaw).

The impedance based medical positioning system 222A determines locations of the electrodes 104 based on capturing and processing signals received from the electrodes 104 and external electrode patches while the electrodes 104 are disposed in a controlled electrical field (e.g., potential field) generated by the electrode patches, for example. The MPS system 222A may include various visualization, mapping and navigation components as known in the art, including, for example, an EnSite™ X EP System commercially available from Abbott Laboratories or as seen generally by reference to U.S. Pat. No. 7,263,397 entitled "Method and Apparatus for Catheter Navigation and Location and Mapping in the Heart" to Hauck et al., or U.S. Patent Publication No. 2007/0060833 A1 to Hauck entitled "Method of Scaling Navigation Signals to Account for Impedance Drift in Tissue", both owned by the common assignee of the present invention, and both hereby incorporated by reference in their entireties.

The magnetic-based medical positioning system 222B determines locations (e.g., P&O) of the magnetic position sensor(s) 10, 10-R in a magnetic coordinate system based on capturing and processing signals received from the magnetic position sensor(s) 10, 10-R while the magnetic position sensor 10, 10-R is disposed in a controlled low-strength alternating current (AC) magnetic (e.g., magnetic) field. The changing or AC magnetic field may induce a current in the coil(s) 14 when the coil(s) 14 are in the magnetic field. The magnetic position sensor(s) 10, 10-R is thus configured to detect one or more characteristics (e.g., flux) of the magnetic field(s) in which it is disposed and generate a signal indicative of those characteristics, which is further processed by medical positioning system 222B to obtain a respective P&O for the magnetic position sensor(s) 10, 10-R relative to, for example, a magnetic field generator.

Figure 8:
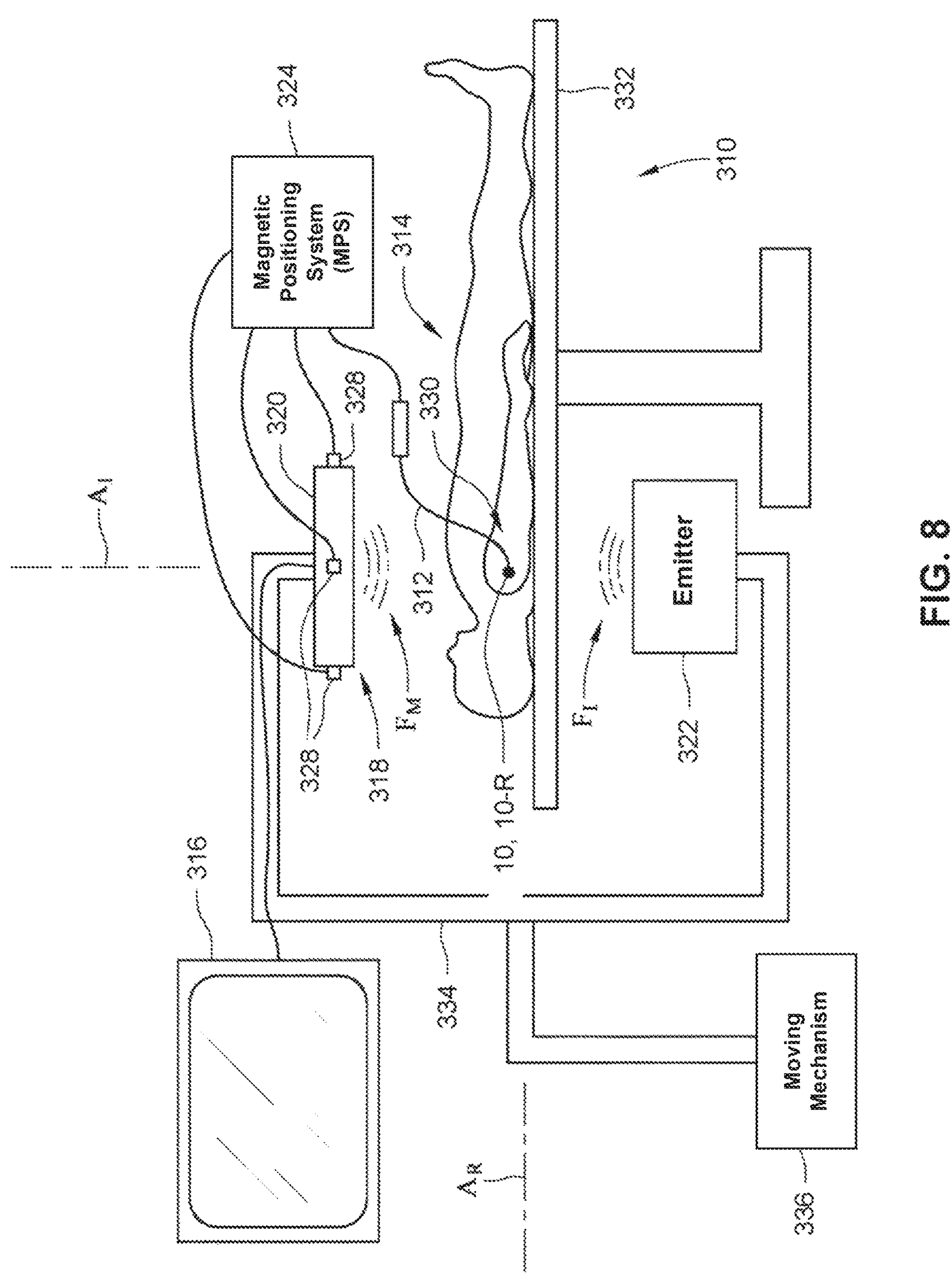
FIG. 8 illustrates another example medical localization system that can be employed in conjunction with a medical device that includes one or more instances of the magnetic position sensor of FIG. 1 and/or one or more instances of the magnetic position sensor of FIG. 3.

FIG. 8 illustrates another example medical positioning system 310 that can be employed in conjunction with a medical device 312 that includes one or more instances of the magnetic position sensor 10, 10-R to determine the position and/or orientations of the magnetic position sensor(s) 10, 10-R within a patient 314 and thereby corresponding location(s) and/or orientations of the medical device 312 within the patient 314. While the medical device 312 is described in the following description as including one magnetic position sensor, the medical device 312 can include more than one instance of the magnetic position sensor 10, 10-R (e.g., 2, 3, 4, 5, or more instances of the magnetic position sensor 10, 10-R) and the system 310 can be process output from any suitable number of the magnetic position sensors 10, 10-R to determine the position and/orientation of the magnetic position sensors 10, 10-R. In some embodiments, the system 310 includes a display 316 and is configured to generate and display a model of an internal tissue surface of the patient 314 on the display 316 based on the determined positions and/or orientations of the magnetic position sensors 10, 10-R. The system 310 includes a moving imager 318, which includes an intensifier 320 and an emitter 322, and a magnetic positioning system (MPS) 324, which includes field generators 328. In some embodiments, the combination of the medical device 312 and the system 310 is configured to generate electrophysiology map information and cardiac mechanical activation data pertaining to the tissue model generated by medical imaging system 310 and display the map information and the activation data on the display 316 to facilitate diagnosis and treatment of the patient 314. As described herein, the magnetic position sensor 10, 10-R may have an improved signal to noise ratio that enhances the accuracy and reliability of the determination of the location and/or orientation of the magnetic position sensor 10, 10-R by the system 310.

The moving imager 318 acquires an image of a region of interest 330 while the patient 314 lies on an operation table 332. The intensifier 320 and the emitter 322 are mounted on a C-arm 334, which is positioned relative to the patient 314 using a moving mechanism 336. In one embodiment, the moving imager 318 includes a fluoroscopic or X-ray type imaging system that generates a two-dimensional (2D) image of the heart of the patient 314.

The magnetic positioning system (MPS) 324 includes magnetic field generators 328. The MPS 324 determines the position and orientation of the magnetic position sensor 10, 10-R of the medical device 312 in a coordinate system based on output from the magnetic positioning sensor 10, 10-R while disposed in magnetic field(s) generated by the magnetic field generators 328. In one embodiment, the MPS 324 includes a MediGuide gMPS magnetic positioning system, as is commercially offered by St. Jude Medical, Inc., that simultaneously generates a three-dimensional (3D) model of the heart of the patient 314.

The C-arm 334 positions the intensifier 320 above the patient 314 and the emitter 322 underneath operation table 332. The emitter 322 generates, and intensifier 320 receives, an imaging field $F_I$, e.g., a radiation field, that generates a 2D image of the area of interest 330 on the display 316. The intensifier 320 and the emitter 322 of the moving imager 318 are connected by the C-arm 334 so as to be disposed at opposites sides of patient 314 along an imaging axis $A_I$, which extends vertically with reference to FIG. 8 in the described embodiment. The moving mechanism 336 rotates the C-arm 334 about a rotation axis $A_R$, which extends horizontally with reference to FIG. 8 in the described embodiment. The moving mechanism 336 or an additional moving mechanism may be used to move the C-arm 334 into other orientations. For example, the C-arm 334 can be rotated about an axis (not shown) extending into the plane of FIG. 8 such that imaging axis $A_I$ is rotatable in the plane of FIG. 8. As such, the moving imager 318 can be associated with a three-dimensional imaging coordinate system having an x-axis (Xp), a y-axis (Yp), and a z-axis (Zp).

The magnetic positioning system (MPS) 324 is positioned to allow the medical device 312 and the field generators 328 to interact with the MPS 324 through the use of appropriate wired and/or wireless technology. The medical device 312 is inserted into the vasculature of the patient 314 such that magnetic position sensor 10, 10-R is located within the area of interest 330. The field generators 328 are mounted to the intensifier 320 so as to be capable of generating a magnetic field ($F_M$) in the area of interest 330 coextensive with the imaging field $F_I$. The MPS 324 is able to detect the position and orientation of the magnetic position sensor 10, 10-R within the magnetic field ($F_M$).

As described herein, the voltage output of magnetic position sensor 10, 10-R is increased via the extended length of the core 12 relative to the coil 14. The increased voltage of the magnetic position sensor 10, 10-R enhances the accuracy and reliability of the determination of the position and orientation of the magnetic position sensor 10, 10-R by the system MPS 222, MPS 324. Furthermore, hardware used within the system 200, 310 may be able to use larger amplification levels and magnetic transmission frequencies, which is beneficial as it lowers the environmental influence on magnetic transmitters, which drives down positional error. Improved signal strength also permits smaller form factors for magnetic position sensor 10, 10-R, while maintaining the same signal output.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A catheter comprising:

an elongated catheter shaft configured to be received within a patient;

a medical assembly coupled with the elongated catheter shaft and configured for use within the patient to diagnose and/or treat a medical condition of the patient; and one or more magnetic position sensors, wherein each of the one or more magnetic positions sensors comprises a magnetically permeable core and a coil, wherein the magnetically permeable core has a central axis and a core length along the central axis, wherein the coil comprises a wire wrapped around the magnetically permeable core and configured to output an electric signal in response to a magnetic field, wherein the coil has a coil length along the central axis that is less than 90 percent of the core length, and wherein the magnetically permeable core consists of a magnetically permeable material selected from a group consisting of mu-metal and a nickel-iron soft ferromagnetic alloy.

2. The catheter of claim 1, wherein the magnetically permeable material is a nickel-iron soft ferromagnetic alloy.

3. The catheter of claim 1, wherein the coil has an outer diameter of less than 0.015 inch.

4. The catheter of claim 1, wherein the coil has a coil resistance less than 250 ohms at 20 degrees Celsius.

5. The catheter of claim 1, wherein the coil comprises 4 wire layers.

6. The catheter of claim 1, wherein the core length is less than 0.160 inch.

7. The catheter of claim 1, wherein the coil length is less than 80 percent of the core length.

8. The catheter of claim 1, wherein the magnetically permeable material is mu-metal.

9. The catheter of claim 1, wherein the coil has an outer diameter of less than 0.012 inch.

10. The catheter of claim 1, wherein the coil has greater than 1000 turns.

11. The catheter of claim 1, wherein the magnetically permeable core has a solid cross section.

12. The catheter of claim 1, wherein the core length is less than 0.200 inch.

13. The catheter of claim 1, wherein the magnetically permeable core extends at least 12 percent of the core length from an end of the coil.

14. The catheter of claim 1, wherein the magnetically permeable core extends at least 20 percent of the core length from an end of the coil.

15. The catheter of claim 1, wherein the magnetically permeable core extends equally from both ends of the coil.

16. The catheter of claim 1, wherein each of the one or more magnetic positions sensors further comprises an encapsulation that encloses the magnetically permeable core and the coil.

17. The catheter of claim 16, wherein the encapsulation has an outer diameter of less than 0.015 inch.

18. The catheter of claim 16, wherein the encapsulation comprises a surrounding outer membrane and an adhesive within the surrounding outer membrane.

19. The catheter of claim 1, further comprising a handle assembly and wherein:

the elongated catheter shaft comprises a flexible shaft and a steerable section;

the handle assembly is drivingly coupled with the steerable section and operable to selectively bend the steerable section; and at least one of the one or more magnetic position sensors is installed within or distal to the steerable section.

20. The catheter of claim 19, wherein:

the one or more magnetic position sensors comprises a first magnetic position sensor and a second magnetic position sensor;

the first magnetic position sensor is installed within the steerable section; and the second magnetic position sensor is installed distal to the steerable section.

* * * * *